US008207293B2

(12) United States Patent
Ronjat et al.

(10) Patent No.: US 8,207,293 B2
(45) Date of Patent: Jun. 26, 2012

(54) PEPTIDES DERIVED FROM MAUROCALCINE USED AS VECTORS FOR INTRACELLULAR ADDRESSING OF MOLECULES OF INTEREST

(75) Inventors: Michel Ronjat, Vaulnaveys le Haut (FR); Michel De Waard, Chambéry (FR)

(73) Assignees: Commissariat a l'Energie Atomique, Paris (FR); Institut National de la Sante et de la Recherche Medicale, Paris (FR)

( * ) Notice: Subject to any disclaimer, the term of this patent is extended or adjusted under 35 U.S.C. 154(b) by 1187 days.

(21) Appl. No.: 11/719,171

(22) PCT Filed: Nov. 14, 2005

(86) PCT No.: PCT/FR2005/002817
§ 371 (c)(1), (2), (4) Date: Oct. 23, 2007

(87) PCT Pub. No.: WO2006/051224
PCT Pub. Date: May 18, 2006

(65) Prior Publication Data
US 2009/0142266 A1    Jun. 4, 2009

(30) Foreign Application Priority Data
Nov. 12, 2004  (FR) ..................... 04 12045

(51) Int. Cl.
A61K 47/42 (2006.01)
A61K 49/00 (2006.01)
C07K 2/00 (2006.01)
C12N 15/63 (2006.01)

(52) U.S. Cl. ........ 530/300; 424/9.1; 435/7.1; 435/320.1
(58) Field of Classification Search ........................ None
See application file for complete search history.

(56) References Cited

U.S. PATENT DOCUMENTS
6,051,429 A    4/2000   Hawley-Nelson et al.

FOREIGN PATENT DOCUMENTS
WO    WO 00/15655    3/2000
WO    WO 01/64724    9/2001
WO    WO 03/106491   12/2003

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of Escherichia coli maltodextrin phosphorylase," FEBS, Jul. 1991, 286(1,2): 125-128.*

Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
International Search Report for PCT/FR2005/002817 filed Nov. 14, 2005.
McKenzie D. L. et al.; "A Potent New Class of Reductively Activated Peptide Gene Delivery Agents"; Journal of Biological Chemistry, American Society of Biolochemical Biologists, Birmingham, US; vol. 275, No. 14; Apr. 7, 2000; pp. 9970-9977, XP002238140.
Yoneda, et al.; "Synthetic Peptides Containing a Region of SV 40 Large T-Antigen Involved in Nuclear Localization Direct the Transport of Proteins into the Nucleus"; Experimental Cell Research; vol. 170, No. 2; 1987; pp. 439-452; XP008062743.
Tabor AB et al.; "Fluorescently Labelled Peptides as Tools for Probing the Structure and Function of a Non-Viral Gene Delivery Vector"; Journal of Peptide Science; vol. 8, No. Suppl., 2002, p. S154; XP008062746.
Park Y et al.; "Synthesis of Sulfhydryl Cross-Linking Poly(Ethylene Glycol)—Peptides and Glycopeptides as Carriers for Gene Delivery"; Bioconjugate Chemistry; vol. 13, 2002, pp. 232-239; XP002335023.
Kwok KY et al.; "In Vivo Gene Transfer Using Sulfhydryl Cross-Linked PEG-Peptide/Glycopeptide DNA-Co-Condensates"; Journal of Pharmaceutical Sciences; vol. 92, No. 6, Jun. 2003; pp. 1174-1185; XP002335022.
Zhu S et al.; "Evolutionary Origin of Inhibitor Cystine Knot Peptides"; The Faseb Journal, Jul. 3, 2003; XP002335024.
Heitz A, et al.; "Solution Structure of the Squash Trypsin Inhibitor MCoTI-II. A New Family for Cyclic Knottins"; Biochemistry, vol. 40, 2001, pp. 7973-7983, XP002335025.
Fajloun Z et al; "Chemical Synthesis and Characterization of Maurocalcine, A Scorpion Toxin that Activates Ca<2+> Release Channel/Ryanodine Receptors"; FEBS Letters, Elsevier Science Publishers, Amsterdam, NL, vol. 469, No. 2-3, Mar. 10, 2000, pp. 179-185, XP004261072.
Esteve E et al; "Transduction of the Scorpion Toxin Maurocalcine into Cells", The Journal of Biological Chemistry, vol. 280, No. 13, Jan. 14, 2005, pp. 12833-12839; XP002335026.

* cited by examiner

Primary Examiner — Julie Ha
(74) Attorney, Agent, or Firm — Alston & Bird LLP

(57) ABSTRACT

A method of intracellular delivery of a substance of interest, including the step of using a maurocalcine-derived peptide vector for transporting said substance of interest into cells is described. The vector including a maurocalcine-derived peptide of sequence (I): $Z\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}\text{-}X_{25}\text{-}X_{26}\text{-}Z'$, wherein $X_1$ and $X_{26}$ each represent a cysteine, $X_2$ to $X_{25}$ each represent an amino acid or are absent, $X_7$, $X_{10}$, $X_{11}$, $X_{12}$, $X_{13}$, $X_{14}$, $X_{15}$ and $X_{16}$ are always present, and $X_{10}$, $X_{11}$, $X_{13}$ and $X_{14}$, each represent a lysine or an arginine, and Z and/or Z' are absent or each represent a sequence of 1 to 35 amino acids, with the exception of the peptide having the sequence SEQ ID NO:1 in the sequence listing attached in the annex.

12 Claims, 14 Drawing Sheets

A

B 2 hours    4 hours    24 hours

C

SEQUENCE LISTING

```
<160> NUMBER OF SEQ ID NOS: 29

<210> SEQ ID NO 1
<211> LENGTH: 33
<212> TYPE: PRT
<213> ORGANISM: Scorpio maurus

<400> SEQUENCE: 1

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 2
<211> LENGTH: 33
<212> TYPE: PRT
<213> ORGANISM: artificial sequence
<220> FEATURE:
<223> OTHER INFORMATION: maurocalcine K8A mutant

<400> SEQUENCE: 2

Gly Asp Cys Leu Pro His Leu Ala Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg
```

<210> SEQ ID NO 3
<211> LENGTH: 33
<212> TYPE: PRT
<213> ORGANISM: artificial sequence
<220> FEATURE:
<223> OTHER INFORMATION: maurocalcine K19A mutant

<400> SEQUENCE: 3

Gly Asp Cys Leu Pro His Leu Lys Leu Cys Lys Glu Asn Lys Asp Cys
1               5                   10                  15

Cys Ser Ala Lys Cys Lys Arg Arg Gly Thr Asn Ile Glu Lys Arg Cys
            20                  25                  30

Arg

<210> SEQ ID NO 4
<211> LENGTH: 33
<212> TYPE: PRT
<213> ORGANISM: artificial sequence
<220> FEATURE:
<223> OTHER INFORMATION: maurocalcine K20A mutant

<400> SEQUENCE: 4

Gly Asp Cys Leu Pro His Leu Lys Leu Cys Lys Glu Asn Lys Asp Cys
1               5                   10                  15

Cys Ser Lys Ala Cys Lys Arg Arg Gly Thr Asn Ile Glu Lys Arg Cys
            20                  25                  30

Arg

<210> SEQ ID NO 5
<211> LENGTH: 33
<212> TYPE: PRT
<213> ORGANISM: artificial sequence
<220> FEATURE:
<223> OTHER INFORMATION: maurocalcine K22A mutant

<400> SEQUENCE: 5

Gly Asp Cys Leu Pro His Leu Lys Leu Cys Lys Glu Asn Lys Asp Cys
1               5                   10                  15

Cys Ser Lys Lys Cys Ala Arg Arg Gly Thr Asn Ile Glu Lys Arg Cys
            20                  25                  30

Arg

<210> SEQ ID NO 6
<211> LENGTH: 33
<212> TYPE: PRT
<213> ORGANISM: artificial sequence
<220> FEATURE:
<223> OTHER INFORMATION: maurocalcine R23A mutant

<400> SEQUENCE: 6

Gly Asp Cys Leu Pro His Leu Lys Leu Cys Lys Glu Asn Lys Asp Cys
1               5                   10                  15

Cys Ser Lys Lys Cys Lys Ala Arg Gly Thr Asn Ile Glu Lys Arg Cys
            20                  25                  30

Arg

<210> SEQ ID NO 7
<211> LENGTH: 33
<212> TYPE: PRT
<213> ORGANISM: artificial sequence
<220> FEATURE:
<223> OTHER INFORMATION: maurocalcine R24A mutant

```
<400> SEQUENCE: 7

Gly Asp Cys Leu Pro His Leu Lys Leu Cys Lys Glu Asn Lys Asp Cys
1               5                   10                  15

Cys Ser Lys Lys Cys Lys Arg Ala Gly Thr Asn Ile Glu Lys Arg Cys
            20                  25                  30

Arg

<210> SEQ ID NO 8
<211> LENGTH: 33
<212> TYPE: PRT
<213> ORGANISM: artificial sequence
<220> FEATURE:
<223> OTHER INFORMATION: maurocalcine T26A mutant

<400> SEQUENCE: 8

Gly Asp Cys Leu Pro His Leu Lys Leu Cys Lys Glu Asn Lys Asp Cys
1               5                   10                  15

Cys Ser Lys Lys Cys Lys Arg Arg Gly Ala Asn Ile Glu Lys Arg Cys
            20                  25                  30

Arg

<210> SEQ ID NO 9
<211> LENGTH: 33
<212> TYPE: PRT
<213> ORGANISM: Pandinus imperator

<400> SEQUENCE: 9

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg

<210> SEQ ID NO 10
<211> LENGTH: 33
<212> TYPE: PRT
<213> ORGANISM: Opistophtalmus carinatis

<400> SEQUENCE: 10

Gly Asp Cys Leu Pro His Leu Arg Cys Lys Glu Asn Asn Asp Cys
1               5                   10                  15

Cys Ser Lys Lys Cys Lys Arg Arg Gly Thr Asn Pro Glu Lys Arg Cys
            20                  25                  30

Arg

<210> SEQ ID NO 11
<211> LENGTH: 33
<212> TYPE: PRT
<213> ORGANISM: Opistophtalmus carinatis

<400> SEQUENCE: 11

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
            20                  25                  30

Arg

<210> SEQ ID NO 12
<211> LENGTH: 33
<212> TYPE: PRT
```

<213> ORGANISM: artificial sequence
<220> FEATURE:
<223> OTHER INFORMATION: maurocalcine D2A mutant

<400> SEQUENCE: 12

Gly Ala Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 13
<211> LENGTH: 33
<212> TYPE: PRT
<213> ORGANISM: artificial sequence
<220> FEATURE:
<223> OTHER INFORMATION: maurocalcine L4A mutant

<400> SEQUENCE: 13

Gly Asp Cys Ala Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 14
<211> LENGTH: 33
<212> TYPE: PRT
<213> ORGANISM: artificial sequence
<220> FEATURE:
<223> OTHER INFORMATION: maurocalcine P5A mutant

<400> SEQUENCE: 14

Gly Asp Cys Leu Ala His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 15
<211> LENGTH: 33
<212> TYPE: PRT
<213> ORGANISM: artificial sequence
<220> FEATURE:
<223> OTHER INFORMATION: maurocalcine H6A mutant

<400> SEQUENCE: 15

Gly Asp Cys Leu Pro Ala Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 16
<211> LENGTH: 33
<212> TYPE: PRT
<213> ORGANISM: artificial sequence
<220> FEATURE:
<223> OTHER INFORMATION: maurocalcine L7A mutant

<400> SEQUENCE: 16

Gly Asp Cys Leu Pro His Ala Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 17
<211> LENGTH: 33
<212> TYPE: PRT
<213> ORGANISM: artificial sequence
<220> FEATURE:
<223> OTHER INFORMATION: maurocalcine L9A mutant

<400> SEQUENCE: 17

Gly Asp Cys Leu Pro His Leu Lys Ala Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 18
<211> LENGTH: 33
<212> TYPE: PRT
<213> ORGANISM: artificial sequence
<220> FEATURE:
<223> OTHER INFORMATION: maurocalcine E12A mutant

<400> SEQUENCE: 18

Gly Asp Cys Leu Pro His Leu Lys Leu Cys Lys Ala Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 19
<211> LENGTH: 33
<212> TYPE: PRT
<213> ORGANISM: artificial sequence
<220> FEATURE:
<223> OTHER INFORMATION: maurocalcine N13A mutant

<400> SEQUENCE: 19

Gly Asp Cys Leu Pro His Leu Lys Leu Cys Lys Glu Ala Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 20
<211> LENGTH: 33
<212> TYPE: PRT
<213> ORGANISM: artificial sequence
<220> FEATURE:
<223> OTHER INFORMATION: maurocalcine D15A mutant

<400> SEQUENCE: 20

Gly Asp Cys Leu Pro His Leu Lys Leu Cys Lys Glu Asn Lys Ala Cys
1               5                   10                  15

Cys Ser Lys Lys Cys Lys Arg Arg Gly Thr Asn Ile Glu Lys Arg Cys
            20                  25                  30

Arg

<210> SEQ ID NO 21

```
<211> LENGTH: 33
<212> TYPE: PRT
<213> ORGANISM: artificial sequence
<220> FEATURE:
<223> OTHER INFORMATION: maurocalcine G25A mutant

<400> SEQUENCE: 21

Gly Asp Cys Leu Pro His Leu Lys Leu Cys Lys Glu Asn Lys Asp Cys
1               5                   10                  15

Cys Ser Lys Lys Cys Lys Arg Arg Ala Thr Asn Ile Glu Lys Arg Cys
            20                  25                  30

Arg

<210> SEQ ID NO 22
<211> LENGTH: 33
<212> TYPE: PRT
<213> ORGANISM: artificial sequence
<220> FEATURE:
<223> OTHER INFORMATION: maurocalcine N27A mutant

<400> SEQUENCE: 22

Gly Asp Cys Leu Pro His Leu Lys Leu Cys Lys Glu Asn Lys Asp Cys
1               5                   10                  15

Cys Ser Lys Lys Cys Lys Arg Arg Gly Thr Ala Ile Glu Lys Arg Cys
            20                  25                  30

Arg

<210> SEQ ID NO 23
<211> LENGTH: 30
<212> TYPE: PRT
<213> ORGANISM: artificial sequence
<220> FEATURE:
<223> OTHER INFORMATION: maurocalcine E29A mutant

<400> SEQUENCE: 23

Leu Pro His Leu Lys Leu Cys Lys Glu Asn Lys Asp Cys Cys Ser Lys
1               5                   10                  15

Lys Cys Lys Arg Arg Gly Thr Asn Ile Ala Lys Arg Cys Arg
            20                  25                  30

<210> SEQ ID NO 24
<211> LENGTH: 33
<212> TYPE: PRT
<213> ORGANISM: artificial sequence
<220> FEATURE:
<223> OTHER INFORMATION: maurocalcine/imperatoxin A chimera

<400> SEQUENCE: 24

Gly Asp Cys Leu Pro His Leu Lys Arg Cys Lys Ala Asp Asn Asp Cys
1               5                   10                  15

Cys Ser Lys Lys Cys Lys Arg Ala Gly Thr Asn Ile Glu Lys Arg Cys
            20                  25                  30

Arg

<210> SEQ ID NO 25
<211> LENGTH: 33
<212> TYPE: PRT
<213> ORGANISM: artificial sequence
<220> FEATURE:
<223> OTHER INFORMATION: maurocalcine/opicalcine 1 chimera

<400> SEQUENCE: 25

Gly Asp Cys Leu Pro His Leu Lys Arg Cys Lys Glu Asn Asn Asp Cys
1               5                   10                  15
```

Cys Ser Lys Lys Cys Lys Arg Ala Gly Thr Asn Ile Glu Lys Arg Cys
            20                  25                  30

Arg

<210> SEQ ID NO 26
<211> LENGTH: 20
<212> TYPE: PRT
<213> ORGANISM: ARTIFICIAL SEQUENCE
<220> FEATURE:
<223> OTHER INFORMATION: synthetic peptide

<400> SEQUENCE: 26

Cys Trp Cys Lys Lys Lys Lys Lys Lys Lys Lys Lys Lys Lys
1               5                   10                  15

Lys Lys Cys Lys
            20

<210> SEQ ID NO 27
<211> LENGTH: 20
<212> TYPE: PRT
<213> ORGANISM: artificial sequence
<220> FEATURE:
<223> OTHER INFORMATION: synthetic peptide

<400> SEQUENCE: 27

Cys Trp Cys Lys Lys Lys Cys Lys Lys Lys Cys Lys Lys Cys Lys
1               5                   10                  15

Lys Lys Cys Lys
            20

<210> SEQ ID NO 28
<211> LENGTH: 20
<212> TYPE: PRT
<213> ORGANISM: artificial sequence
<220> FEATURE:
<223> OTHER INFORMATION: synthetic peptide

<400> SEQUENCE: 28

Cys Trp Lys Lys Lys Lys Lys Cys Lys Lys Lys Lys Cys Lys Lys
1               5                   10                  15

Lys Lys Lys Cys
            20

<210> SEQ ID NO 29
<211> LENGTH: 34
<212> TYPE: PRT
<213> ORGANISM: Momordica cochinchinensis

<400> SEQUENCE: 29

Ser Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
            20                  25                  30

Cys Gly

PEPTIDES DERIVED FROM MAUROCALCINE USED AS VECTORS FOR INTRACELLULAR ADDRESSING OF MOLECULES OF INTEREST

CROSS REFERENCE TO RELATED APPLICATIONS

This application is a national stage application filed under 35 USC 371 of International Application No. PCT/FR2005/002817, filed Nov. 14, 2005, which claims priority from French patent application 04/12045 filed Nov. 12, 2004.

FIELD AND BACKGROUND OF THE INVENTION

The present invention relates to peptides derived from maurocalcine capable of penetrating into cells and transporting molecules of interest into these cells.

The problem of the transport of substances, in particular of macromolecules with pharmacological properties, through the plasma membrane and of the access thereof to the various intracellular compartments, in particular the cytoplasmic and nuclear compartments, is an obstacle for biotechnological and biomedical research, and for the pharmaceutical industry.

Among the means currently known for introducing the substances into cells, translocation peptides, also known as CPPs (Cell-Penetrating Peptides) represent particularly advantageous vectors (for a review see, in particular, Prochiantz, Curr. Opin. Cell. Biol., 2000, 12, 400-406; Lindgren et al., Trends Pharmacol. Sci., 2000, 21, 99-102).

Indeed, these small molecules are capable of crossing cell membranes in a transporter- and receptor-independent manner and of transporting macromolecules to which said membranes are impermeable, such as proteins and nucleic acids, at low concentration, without energy, efficiently (transduction of 100% of the cells) and rapidly (of the order of 5 to 15 min), in all cell types, in vivo and in vitro. In addition, it has been shown that some of these peptides are capable of crossing the blood-meningeal barrier (Schwarze and Dowdy, Science, 1999, 285, 1569-1572).

These vectors, which consist of a peptide capable of crossing membranes in a transporter- and receptor-independent manner, are different than other vectors comprising a glycopeptide or a peptide coupled to PEG, in which the positively charged peptide serves to condense the DNA and the PEG or the sugar allows targeting of the cells of interest, in particular by binding of the DNA/glycopeptide complex to the receptor for mannose or asialoglycoprotein (peptides $CWCK_{15}CK$, $CW(CK_3)_4CK$ and $CWK_5CK_5CK_5C$ (SEQ ID Nos. 26 to 28): Park et al., Bioconjugate Chem., 2002, 13, 232-239; Kwok et al., J. Pharm. Sciences, 2003, 92, 1174-1185).

The penetrating peptides currently known are divided up into two categories:
peptides derived from membrane translocation signal sequences of various proteins (Kaposi's sarcoma-derived fibroblast growth factor (K-FGF) and immunoglobulin light chain (Ig(v)); the mechanism of penetration of these peptides is unknown, the central hydrophobic region is involved in penetration but the structure of this region varies according to the proteins (alpha-helix (K-FGF) or beta-sheet (Ig(v));
peptides derived from intercellular signaling proteins or "messenger proteins"; these proteins have the particularity of penetrating directly into cells and of reaching the nucleus, where they regulate transcription (HIV-1 Tat, HSV-1 VP22 and homeoproteins).

Functional studies have made it possible to identify minimum sequences required and sufficient for the translocation of each of these peptides:
the smallest homeoprotein fragment capable of crossing membranes and of serving as a vector to other proteins or to oligonucleotides is the 43-58 peptide, known as penetratin, corresponding to helix 3 of the homeodomain (Derossi et al., J. Biol. Chem., 1994, 269, 10444-10450 and international application WO 97/12912). The study of mutants of this sequence has shown that the alpha-helix structure is not involved in intracellular translocation, but plays a role in nuclear addressing. On the other hand, the W residue at position 48 is important and the amphiphilic properties of the peptide are necessary but not sufficient for the translocation. Supplementary studies have confirmed the role of the W48 residue and shown the importance of the interaction of positively charged amino acids (lysines and arginines) with the membrane phospholipids, which are negatively charged. These studies have led to the inverse micelle model being proposed. According to this model, penetratins are stabilized at the cell surface by electrostatic interactions and the tryptophan at position 48 forces the formation of an inverse micelle which traps the peptide and delivers it into the cytoplasm;
the 267-300 fragment of the VP22 protein corresponds to the minimum sequence for internalization (Elliot and O'Hare, Cell, 1997, 88, 223-233);
the most effective fragment of the Tat protein is the 48-60 fragment, which corresponds to the entire basic region and includes the nuclear localization signal. However, a shorter fragment (47-57) is capable of transporting, in the form of a fusion protein, proteins of 15 to 120 kDa, in various cell types, in vitro and in vivo, and is capable of crossing the blood-meningeal barrier. In addition, unlike the Tat peptide of the human virus, the Tat peptide of the equine virus has a structure similar to that of a homeodomain.

These functional studies have not made it possible to identify a general mechanism of penetration of these peptides, which would make it possible in particular to identify the common sequence and/or structural elements responsible for the translocation of these peptides.

Maurocalcine (MCa) is a 33 amino acid toxin isolated from the venom of the scorpion *Scorpio maurus palmatus*, corresponding to the sequence SEQ ID No. 1 in the sequence listing attached in the annex. The corresponding cDNA encodes a 66 amino acid precursor comprising 3 domains: an N-terminal signal peptide of 22 amino acids, followed by a propeptide of 11 amino acids, which is rich in negatively charged amino acids and ends with a cleavage signal characteristic of prohormones (KR), and a C-terminal peptide of 33 amino acids corresponding to the mature peptide (maurocalcine). Maurocalcine exhibits strong homology with the toxin of two other scorpions: imperatoxin of *Pandinus imperator* (IpTx A, SEQ ID No. 9; 82% identity) and opicalcines 1 and 2 of *Opistophthalmus carinatis* (SEQ ID Nos. 10 and 11; 91% and 88% identity, respectively; FIG. 1A).

It also exhibits homology, over a 6 amino acid motif comprising a succession of basic residues, followed by a serine or by a threonine ($K_{19}K_{20}$-$K_{22}R_{23}R_{24}$-$T_{26}$), with the activator domain of the II-III loop of the dihydropyridine receptor (DHPR), an L-type voltage-dependent calcium channel. In skeletal muscle, the dihydropyridine receptor—located on the plasma membrane—and the ryanodine receptor type 1 (RyR1)—located in the vesicles of the sarcoplasmic reticulum—form part of the calcium mobilization complex, which is involved in excitation-contraction coupling. Maurocalcine is one of the most potent effectors of the ryanodine receptor type 1 (RyR1); it has in particular been shown that it stimulates the binding of ryanodine to the RyR1 receptor, that it induces considerable modifications in the opening of the calcium channel, characterized by the appearance of prolonged periods of subconductance, and that the extracellular addition of maurocalcine to myotube cultures induces calcium release from the sarcoplasmic reticulum to the cytoplasm (Fajloun et al., FEBS Letters, 2000, 469, 179-185; Estève et al., J. Biol. Chem., 2003, 278, 37822-37831). Thus it has been proposed to use maurocalcine or analogs thereof comprising the KKCKKR motif, as an active ingredient for inducing immunosuppression or treating pathologies related to a calcium channel dysfunction (PCT international application WO 01/64724).

The three-dimensional structure of maurocalcine corresponds to folding according to the ICK motif (Inhibitor Knot Motif), present in many plant, animal or fungal peptides; the ICK family encompasses peptides of different sequences and of varied biological activities, such as animal toxins (snake or spider venom) and protease inhibitors of plant origin, for instance the McoT I-II peptide (SGSDGGVCPKILKKCR-RDSDCPGACICRGNGYCG (SEQ ID No. 29)) (Zhu et al., The Faseb Journal, 3 Jul. 2003; Heitz et al., Biochemistry, 2001, 40, 7973-7983).

The structure of maurocalcine consists more specifically of: (i) a compact core which is linked by disulfide bridges ($C_3$-$C_{17}$, $C_{10}$-$C_{21}$ and $C_{16}$-$C_{32}$) and which includes three beta-sheets (9-11, 20-33 and 30-33; the sheets 20-33 and 30-33 being anti-parallel), and (ii) an emerging loop at the N-terminal end (Mobash et al., Proteins, 2000, 40, 436-442). It is represented as a molecule comprising a positively charged face which could represent a surface of interaction with the RyR1 receptor (Mobash et al., mentioned above). In addition, the study of maurocalcine mutants (K8A, K19A, K20A, K22A, R23A, R24A and T26A; SEQ ID Nos. 2 to 8) has shown that the R24 residue is important for the effects of maurocalcine on the binding of ryanodine to the RyR1 receptor (Estève et al., mentioned above).

During the course of their study of the effector role of maurocalcine on the ryanodine receptor type 1 (RyR1), the inventors have shown that maurocalcine, which does not belong to any of the categories of proteins containing CPPs mentioned above, is capable of penetrating into cells in vitro and of transporting a protein.

The inventors have now sought to define the minimal characteristics of the amino acid sequences derived from maurocalcine that are capable of serving as a vector for the internalization and addressing of substances of interest, in particular macromolecules of interest such as proteins and nucleic acids, and particles comprising chemical molecules of interest. In addition, since maurocalcine is a toxin with known pharmacological properties, it cannot be used in vivo. Consequently, the inventors have also given themselves the aim of obtaining maurocalcine-derived peptide vectors which are preferably not toxic in vivo, i.e. which do not have a pharmacological activity on the RyR1 receptor, in particular due to the fact that they do not bind to said RyR1 receptor.

SUMMARY OF THE INVENTION

Consequently, a subject of the present invention is the use of a peptide vector for the intracellular addressing of a substance of interest, characterized in that said vector consists essentially of a maurocalcine-derived peptide corresponding to the following sequence (I):

$Z$-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$-$X_{25}$-$X_{26}$-$Z'$
(I), in which:
  $X_1$ and $X_{26}$ each represent a cysteine,
  $X_2$ to $X_{25}$ each represent an amino acid or are absent, $X_7$, $X_{10}$, $X_{11}$, $X_{12}$, $X_{13}$, $X_{14}$, $X_{15}$ and $X_{16}$ always being present, and
  $X_{10}$, $X_{11}$, $X_{13}$ and $X_{14}$ each represent a lysine or an arginine,
and
  Z and/or Z' are absent or each represent a sequence of 1 to 35 amino acids, with the exception of the peptide having the sequence SEQ ID No. 1, in the sequence listing attached in the annex.

The invention encompasses the use of maurocalcine-derived peptides such as, in particular, natural or synthetic variants of maurocalcine, for example maurocalcine analogs. The invention also encompasses the use of chimers between maurocalcine and a toxin comprising an ICK motif, for instance opicalcine (1 or 2) and imperatoxin A.

For the purpose of the present invention, the term "amino acid" is intended to mean a natural or synthetic amino acid, i.e.: the 20 natural α-amino acids commonly found in proteins (A, R, N, D, C, Q, E, G, H, I, L, K, M, F, P, S, T, W, Y and V), certain amino acids rarely encountered in proteins (hydroxyproline, hydroxylysine, methyllysine, dimethyllysine, etc.), amino acids which do not exist in proteins, for instance β-alanine, γ-aminobutyric acid, homocysteine, ornithine, citrulline, canavanine, norleucine or cyclohexylalanine, and also the enantiomers and diastereoisomers of the above amino acids.

The peptide as defined in the present invention is capable of penetrating into any cell type in vitro or in vivo, and of transporting substances of interest such as macromolecules to which the cell is impermeable (proteins, nucleic acids) and particles comprising chemical molecules of interest, into cell compartments, more particularly the cytoplasmic compartment and the nuclear compartment. For example, complexes between the peptide according to the invention and substances such as proteins whose molecular weight ranges up to at least 60 kDa and nanoparticles are transported into the cytoplasm and the nucleus of cells.

This property can be readily verified by incubation of said peptide bound to said substance, in the presence of said cells, and detection of the presence of said peptide and/or of said substance in the cells, in particular by analysis of specific labeling of said peptide and/or of said substance, by any technique known to those skilled in the art, in particular by microscopy.

Consequently, said peptide can be used as a vector for the intracellular addressing of substances capable of interacting with an intracellular target. These substances are, in particular, pharmacologically active substances whose target is intracellular; these drugs are in particular medicaments or plant-protection products. These substances may also be ligands of an intracellular component to be detected (endogenous or pathogenic molecule), in particular antibodies or antibody fragments (Fab, Fv or scFv), which can be used as an intracellular molecular probe. Said substances include chemical molecules, in particular macromolecules: proteins, peptides, peptide nucleic acids (PNAs), nucleic acids (plasmids, oligonucleotides, antisense nucleic acids, siRNAs) and particles, in particular nanoparticles or liposomes comprising chemical molecules of interest, encapsulated in or grafted (coupled) to said particles.

Thus, said peptide has many applications in the biotechnology field, especially nanobiotechnology field, in particular for the diagnosis and treatment of human or animal pathologies (biomedical applications) and as a tool for research in these fields.

In order to implement the present invention, the substance to be transported is coupled to the peptide vector by any appropriate means, known itself, that makes it possible to associate a peptide with a substance (peptide, protein, nucleic acid or other chemical molecule).

When said substance to be transported is a peptide or a protein, it is advantageously coupled to the peptide vector by a peptide bond.

Said substance can also be coupled to the peptide vector noncovalently, in particular by means of streptavidin-biotin complexes, for example the peptide vector is biotinylated and the substance of interest is coupled to streptavidin.

Said substance and said peptide vector can also be incorporated into the same particle; they can in particular be coupled to nanoparticles or liposomes.

In addition, when said vector is used for detecting an intracellular component (intracellular molecular probe), it can advantageously be coupled to an appropriate label, to labeled particles, or else to a labeled substance. The labeling is in particular fluorescent labeling or magnetic labeling, detectable by any technique known to those skilled in the art (fluorescence microscopy, flow cytometry, magnetic resonance imaging).

Such intracellular molecular probes have applications in cell imaging in vitro and in vivo, in particular real-time imaging. They can in particular be used as a reagent for diagnosing a genetic or acquired disease or an infection with a microorganism, or as a research tool.

According to an advantageous embodiment of said use, $X_{15}$ is different than an arginine and than a lysine; this mutation makes it possible to abolish the binding of said peptide to the RyR1 receptor and to abolish the pharmacological effects resulting from this binding.

According to another advantageous embodiment of said use, $X_7$ and/or $X_{12}$ represent a cysteine.

According to another advantageous embodiment of said use, $X_2, X_3, X_4, X_5, X_6, X_8, X_{23}, X_{24}$ and $X_{25}$ are absent.

According to an advantageous arrangement of said use, $X_{17}$ to $X_{22}$ are present and $X_{21}$ and/or $X_{22}$ represent an arginine or a lysine, preferably $X_{21}$ represents a lysine.

According to another advantageous embodiment of said use, Z' represents an arginine or a lysine.

According to another advantageous embodiment of said use, Z corresponds to the following sequence (II):
$Z_1$-$Z_2$-$Z_3$-$Z_4$-$Z_5$-$Z_6$-$Z_7$-$Z_8$-$Z_9$-$Z_{10}$-$Z_{11}$-$Z_{12}$-$Z_{13}$-$Z_{14}$-$Z_{15}$-$Z_{16}$-$Z_{17}$-$Z_{18}$-$Z_{19}$-$Z_{20}$-$Z_{21}$-$Z_{22}$-$Z_{23}$-$Z_{24}$-$Z_{25}$-$Z_{26}$-$Z_{27}$-$Z_{28}$-$Z_{29}$-$Z_{30}$-$Z_{31}$-$Z_{32}$-$Z_{33}$-$Z_{34}$-$Z_{35}$ (II), in which: $Z_1$ to $Z_{35}$ each represent an amino acid or are absent, with $Z_{29}, Z_{30}, Z_{32}$ and $Z_{31}$ or $Z_{33}$ always being present.

According to an advantageous arrangement of this embodiment, $Z_{21}$ and/or $Z_{29}$ represent a cysteine; preferably, when $Z_{21}$ represents a cysteine, then $X_7$ also represents a cysteine, and when $Z_{29}$ represents a cysteine, then $X_{12}$ also represents a cysteine. Preferably $X_7, X_{12}, Z_{21}$ and $Z_{29}$ each represent a cysteine.

According to another advantageous arrangement of this embodiment, at least one amino acid chosen from $Z_{30}, Z_{31}, Z_{32}, Z_{33}, Z_{34}$ and $Z_{35}$ represents a lysine or an arginine; preferably, $Z_{30}$ and/or $Z_{34}$ represent an arginine or a lysine.

According to another advantageous arrangement of this embodiment, at least one amino acid chosen from $Z_{22}, Z_{23}, Z_{24}, Z_{25}, Z_{26}, Z_{27}$ and $Z_{28}$ represents a lysine or an arginine; preferably $Z_{27}$ and/or $Z_{28}$ represent an arginine or a lysine.

Preferably, at least three amino acids chosen from $Z_{22}, Z_{23}, Z_{24}, Z_{25}, Z_{26}, Z_{27}, Z_{28}, Z_{30}, Z_{31}, Z_{32}, Z_{33}, Z_{34}$ and $Z_{35}$ each represent a lysine or an arginine. Even more preferably, $Z_{27}$ and $Z_{30}$ each represent a lysine and $Z_{28}$ or $Z_{34}$ each represents a lysine or an arginine.

According to another advantageous arrangement of this embodiment, at least $Z_1$ to $Z_{18}, Z_{22}$, and $Z_{31}$ or $Z_{34}$ are absent. Preferably, the following residues are absent: $Z_1$ to $Z_{18}, Z_{22}$ and $Z_{31}$ or $Z_{34}$; $Z_1$ to $Z_{19}, Z_{22}$ and $Z_{31}$ or $Z_{34}$; $Z_1$ to $Z_{20}, Z_{22}$ and $Z_{31}$ or $Z_{34}$; $Z_1$ to $Z_{26}$ and $Z_{31}$ or $Z_{34}$, $Z_1$ to $Z_{28}$ and $Z_{31}$ or $Z_{34}$.

For example, one of the following amino acid sequences is present: $Z_{19}$ to $Z_{21}, Z_{23}$ to $Z_{30}$ and $Z_{32}$ to $Z_{35}$; $Z_{19}$ to $Z_{21}, Z_{23}$ to $Z_{33}$ and $Z_{35}$; $Z_{20}, Z_{21}, Z_{23}$ to $Z_{30}$ and $Z_{32}$ to $Z_{35}$; $Z_{20}, Z_{21}, Z_{23}$ to $Z_{33}$ and $Z_{35}$; $Z_{21}, Z_{23}$ to $Z_{30}$ and $Z_{32}$ to $Z_{35}$; $Z_{21}, Z_{23}$ to $Z_{33}$ and $Z_{35}$.

According to another advantageous embodiment of said use, the peptide of sequence (I) consists of D amino acids.

Peptides in accordance with the present invention are represented in particular by:
a) chimeras between maurocalcine and imperatoxin or maurocalcine and opicalcine, for instance the peptides of sequence SEQ ID Nos. 24 and 25,
b) maurocalcine-derived peptides of 33 amino acids in which:
   $X_1, X_7, X_{12}, X_{26}, Z_{21}$ and $Z_{29}$ represent C,
   $X_{10}, X_{11}, X_{13}, X_{14}, X_{21}, X_{22}, Z_{27}, Z_{30}$, and $Z_{28}$ or $Z_{34}$ represent K or R; preferably, at least $X_{10}, X_{11}, X_{13}, X_{21}, Z_{27}$ and $Z_{30}$ represent K, even more preferably $X_{10}, X_{11}, X_{13}, X_{21}, Z_{27}$ and $Z_{30}$ represent K and $Z_{28}$ or $Z_{34}$ represent K or R, preferably $Z_{28}$ represents R or $Z_{34}$ represents K,
   $X_2, X_3, X_4, X_5, X_6, X_8, X_{23}, X_{24}, X_{25}, Z_1$ to $Z_{18}, Z_{22}$, and $Z_{31}$ or $Z_{34}$ are absent,
   $X_9$ represents S or G,
   $X_{15}$ represents R,
   $X_{17}$ represents T, S or A,
   $X_{19}$ represents a hydrophobic amino acid selected from: A, V, L, I, P, W, F and M,
   $X_{16}, X_{18}, X_{20}, Z_{19}, Z_{20}, Z_{23}, Z_{24}, Z_{25}, Z_{26}, Z_{32}, Z_{33}, Z_{35}, Z'$, and optionally $Z_{28}, Z_{31}, Z_{34}$, represent A, C, D, E, F, G, K, L, M, P or N, preferably A or F; for example $Z_{19}$ represents G, and Z' represents R or K,
c) the fragments of the peptides defined in b) corresponding to positions 16 to 32 or 16 to 33 of maurocalcine,
d) the fragments of the peptides defined in b) corresponding to positions 10 to 32 or 10 to 33 of maurocalcine,
e) the fragments of the peptides defined in b) corresponding to positions 8 to 32 or 8 to 33 of maurocalcine; and
f) the peptides derived from the peptides defined in b), c), d) and e) in which $X_{15}$ is different than R and than K.

Among these peptides, mention may be made of those which have the sequences SEQ ID Nos. 2 to 23.

According to another advantageous embodiment of said use, said peptide vector is coupled to an appropriate label, in particular a fluorochrome; the coupling may be covalent or noncovalent, in particular by means of labeled streptavidin-biotin complexes or labeled particles.

According to yet another advantageous embodiment of said use, the peptide vector as defined above is coupled to particles, in particular nanoparticles; advantageously, said particles are labeled and/or they comprise a substance of interest, such as a pharmacologically active substance, that can be used in particular as a medicament or a plant-protection product, or else a substance that is a ligand of an intracellular component to be detected, that can be used as an intracellular molecular probe.

According to another advantageous embodiment of said use, the sequence (I) of the peptide vector as defined above is fused to a heterologous peptide or polypeptide sequence of interest, so as to form a chimeric peptide or protein.

The term "heterologous" is intended to mean a sequence other than that which is directly adjacent to the sequence (I), in the sequence of maurocalcine or of a maurocalcine analog.

Said chimeric peptide or said chimeric protein are advantageously coupled to an appropriate label and/or to particles, it being possible for said particles to be optionally labeled.

The insertion of the sequence (I) into the peptide or the protein of interest is carried out at the $NH_2$ or COOH end or at an appropriate internal site, which site is chosen according to the structure of said protein or of said peptide.

The subject of the present invention is also a composition comprising a pharmacologically active substance whose target is intracellular and a peptide vector as defined above, as a vector for intracellular addressing of said substance.

According to an advantageous embodiment of said composition, said pharmacologically active substance and said peptide vector are in the form of a chimeric peptide or protein as defined above.

According to an advantageous embodiment of said composition, it comprises particles comprising both said pharmacologically active substance and said peptide vector.

According to yet another advantageous embodiment of said composition, said pharmacologically active substance is a medicament intended to be administered to a human or animal individual.

A subject of the present invention is also the composition as defined above, as a medicament.

A subject of the present invention is also the use of a composition as defined above, for the preparation of a medicament for use in the treatment of a pathology in humans or animals.

A subject of the present invention is also a composition comprising a ligand of an intracellular component to be detected (intracellular probe) and a peptide vector as defined above, as a vector for intracellular addressing of said ligand.

According to an advantageous embodiment of said composition, said peptide vector is coupled to an appropriate label, to labeled nanoparticles, and/or to said ligand (chimeric protein or peptide), as specified above.

According to another advantageous embodiment of said composition, said ligand is an antibody or a functional fragment of an antibody directed against said component.

A subject of the present invention is also the composition as defined above, as a diagnostic reagent.

A subject of the present invention is also a method of treating a pathology, characterized in that it comprises the administration of a composition as defined above, to an individual, by any appropriate means.

A subject of the present invention is also an in vitro method of detecting an intracellular component, characterized in that it comprises:
  bringing a cell sample into contact with a detection reagent as defined above, and
  detecting an intracellular labeling, by any appropriate means.

In accordance with the invention, said cell sample comprises cells of a higher eukaryotic organism, possibly infected with a microorganism, or else cells of a microorganism (bacterium, yeast, fungus, parasite).

A subject of the present invention is also an in vivo method of detecting an intracellular component, characterized in that it comprises:
  introducing a detection reagent as defined above into an organism, and
  detecting an intracellular labeling in situ, by any appropriate means.

According to an advantageous embodiment of said methods, said detection reagent is a labeled reagent as defined above. Said reagent is, for example, coupled to a fluorochrome, or to particles coupled to a fluorochrome.

In accordance with the invention, said organism is a higher eukaryote, in particular a human being, an animal or a plant.

A subject of the present invention is also a chimeric peptide or protein as defined above, said chimeric peptide or said chimeric protein being optionally labeled.

A subject of the present invention is also a peptide of sequence (I) as defined above, with the exception of the peptides SEQ ID Nos. 1 to 11 and 26 to 29; said peptide can advantageously be labeled.

A subject of the present invention is particles coupled to a peptide vector as defined above; said particles and/or said vector can advantageously be labeled. Said particles are advantageously nanoparticles.

A subject of the present invention is also a polynucleotide encoding the peptide vector, or else the fusion peptide or protein as defined above. In accordance with the invention, the sequence of said polynucleotide (DNA or RNA) corresponds to that of the cDNA encoding said peptide vector or else encoding said fusion peptide or said fusion protein. The sequence of said polynucleotide can comprise a signal peptide for translocation into the endoplasmic reticulum, so as to produce a peptide vector/fusion peptide or protein secreted into the extracellular medium. Said signal peptide can in particular be that of maurocalcine or of any peptide or protein capable of being secreted into the extracellular medium. In addition, the sequence of said polynucleotide can also comprise the 11-amino acid sequence of the maurocalcine propeptide or of another peptide of the ICK family, inserted 5' of the cDNA sequence encoding said peptide vector.

Said sequence can advantageously be modified in such a way that the codon usage is optimal in the host in which it is expressed.

The subject of the present invention encompasses in particular:
a) expression cassettes comprising at least one polynucleotide as defined above, under the control of appropriate regulatory sequences for transcription and, optionally, for translation (promoter, activator, intron, initiation codon (ATG), stop codon, polyadenylation signal), and
b) recombinant vectors comprising a polynucleotide in accordance with the invention. Advantageously, these vectors are expression vectors comprising at least one expression cassette as defined above.

A subject of the present invention is also prokaryotic or eukaryotic host cells modified with at least one polynucleotide or one recombinant vector as defined above.

A subject of the present invention is also a transgenic nonhuman mammal, characterized in that all or part of its cells are modified with a polynucleotide or a recombinant vector as defined above.

A subject of the present invention is also a transgenic plant, characterized in that all or part of its cells are modified with a polynucleotide or a recombinant vector as defined above.

Many nucleic acid vectors into which it is possible to insert a nucleic acid molecule of interest in order to introduce it into and maintain it in a eukaryotic or prokaryotic host cell, are known in themselves; the choice of an appropriate vector depends on the use envisioned for this vector (for example, replication of the sequence of interest, expression of this sequence, maintenance of this sequence in extrachromosomal form, or else integration into the chromosomal material of the host), and also on the nature of the host cell. For example, it is possible to use, inter alia, viral vectors such as adenoviruses, retroviruses, lentiviruses, AAVs and baculoviruses, into which the sequence of interest has been inserted beforehand; it is also possible to associate said sequence (isolated or inserted into a plasmid vector) with a substance that allows it to cross the host cell membrane, such as a transporter, for instance a nanotransporter or a preparation of liposomes, or of cationic polymers, or else to introduce it into said host cell using physical methods such as electroporation or microinjection. In addition, these methods can advantageously be combined, for example using electroporation associated with liposomes.

The polynucleotides, the recombinant vectors and the transformed cells as defined above can be used in particular for the production of the fusion peptides and proteins according to the invention.

The polynucleotides according to the invention are obtained by the conventional methods, known in themselves, according to the standard protocols such as those described in *Current Protocols in Molecular Biology* (*Frederick M. AUSUBEL, 2000, Wiley and son Inc., Library of Congress, USA*). For example, they can be obtained by amplification of a nucleic sequence by PCR or RT-PCR, by screening genomic DNA libraries by hybridization with a homologous probe, or else by total or partial chemical synthesis. The recombinant vectors are constructed and introduced into host cells by conventional recombinant DNA and genetic engineering methods, which are known in themselves.

The peptides and their derivatives (fusion peptides and proteins) are prepared by conventional techniques known to those skilled in the art:
the maurocalcine-derived peptides and the fusion peptides can be solid-phase synthesized according to the Fmoc technique, originally described by Merrifield et al. (J. Am. Chem. Soc., 1964, 85: 2149-) and purified by reverse-phase high performance liquid chromatography,
the maurocalcine-derived peptides, and also the fusion peptides and proteins, can also be produced from the corresponding cDNAs, obtained by any means known to those skilled in the art; the cDNA is cloned into a eukaryotic or prokaryotic expression vector and the protein or the fragment produced in the host cells modified by the recombinant vector is purified by any appropriate means, in particular by affinity chromatography.

BRIEF DESCRIPTION OF THE DRAWINGS

In addition to the above arrangements, the invention also comprises other arrangements which will emerge from the description that follows, which refers to examples of use of the peptides according to the present invention and also to the table hereinafter, summarizing the sequences of the application, and to the attached drawings in which.

TABLE I

Figure 1:
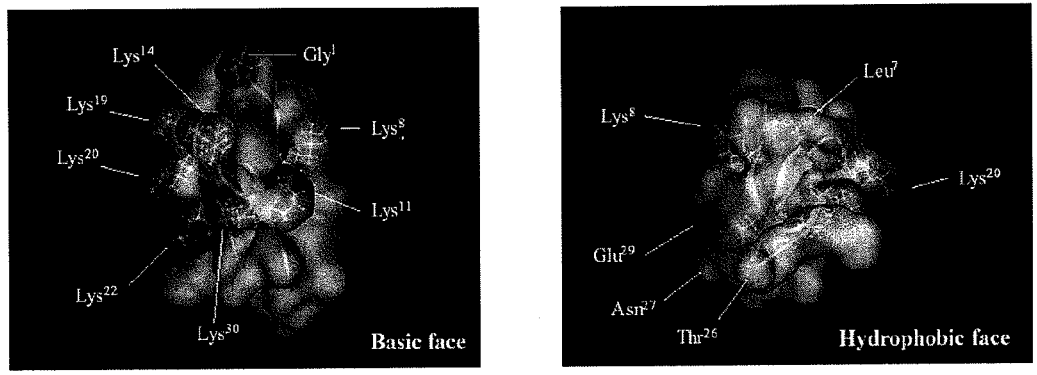
FIG. 1 represents the sequence and the structure of maurocalcine. A. Alignment of the sequences of maurocalcine and of two other analogous toxins, also active on the ryanodine receptor: opicalcine 1 and imperatoxin A. All the toxins have the same number of positively charged amino acids or basic amino acids (12 positively charged amino acids out of a total of 33 amino acids). B. Three-dimensional structure of maurocalcine, established using the WEBLAB® VIEWER-PRO™ software. Left panel: basic face including the positively charged residues ($G_1$, $K_8$, $K_{11}$, $K_{14}$, $K_{19}$, $K_{20}$, $K_{22}$ and $K_{30}$). Right panel: hydrophobic face which illustrates the absence of positively charged residues on the opposite face of the molecule. The peptide backbone is represented by a ribbon, whereas the side chains of the positively charged amino acids are indicated by balls and stems represented to scale.

| | | sequence listing | |
|---|---|---|---|
| Identifier number | NCBI accession number | Peptide | Sequence |
| SEQ ID NO: 1 | 1C6WA | Maurocalcine[1] (MCa) | GDCLPHLKLCKENKDCCSKKCKRRGTNIEKRCR |
| SEQ ID NO: 2 | — | Mutant MCa K8A | GDCLPHL<u>A</u>LCKENKDCCSKKCKRRGTNIEKRCR |

TABLE I-continued sequence listing

| Identifier number | NCBI accession number | Peptide | Sequence |
|---|---|---|---|
| SEQ ID NO: 3 | — | Mutant MCa K19A | GDCLPHLKLCKENKDCCSAKCKRRGTNIEKRCR |
| SEQ ID NO: 4 | — | Mutant MCa K20A | GDCLPHLKLCKENKDCCSKACKRRGTNIEKRCR |
| SEQ ID NO: 5 | — | Mutant MCa K22A | GDCLPHLKKCKENKDCCSKKCARRGTNIEKRCR |
| SEQ ID NO: 6 | — | Mutant MCa R23A | GDCLPHLKLCKENKDCCSKKCKARGTNIEKRCR |
| SEQ ID NO: 7 | — | Mutant MCa R24A | GDCLPHLKLCKENKDCCSKKCKRAGTNIEKRCR |
| SEQ ID NO: 8 | — | Mutant MCa T26A | GDCLPHLKLCKENKDCCSKKCKRPGANIEKRCR |
| SEQ ID NO: 9 | P59868 | Imperatoxin A[2] (IpTxA) | GDCLPHLKRCKADNDCCGKKCKRRGTNAEKRCR |
| SEQ ID NO: 10 | P60252 | Opicalcine 1 (OPi) | GDCLPHLKRCKENNDCCSKKCKRRGTNPEKRCR |
| SEQ ID NO: 11 | P60253 | Opicalcine 2 (OPi) | GDCLPHLKRCKENNDCGSKKCKRRGANPEKRCR |
| SEQ ID NO: 12 | — | Mutant MCa D2A | GACLPHLKLCKENKDCCSKKCKRRGTNIEKRCR |
| SEQ ID NO: 13 | — | Mutant MCa L4A | GDCAPHLKLCKENKDCCSKKCKRRGTNIEKRCR |
| SEQ ID NO: 14 | — | Mutant MCa P5A | GDCLAHLKLCKENKDCCSKKCKRRGTNIEKRCR |
| SEQ ID NO: 15 | — | Mutant MCa H6A | GDCLPALKLCKENKDCCSKKCKRRGTNIEKRCR |
| SEQ ID NO: 16 | — | Mutant MCa L7A | GDCLPHAKLCKENKDCCSKKCKRRGTNIEKRCR |
| SEQ ID NO: 17 | — | Mutant MCa L9A | GDCLPHLKACKENKDCCSKKCKRRGTNIEKRCR |
| SEQ ID NO: 18 | — | Mutant MCa E12A | GDCLPWLKLCKANKDCCSKKCKRRGTNIEKRCR |
| SEQ ID NO: 19 | — | Mutant MCa N13A | GDCLPHLKLCKEAKDCCSKKCKRRGTNIEKRCR |
| SEQ ID NO: 20 | — | Mutant MCa D15A | GDCLPHLKLCKENKACCSKKCKRRGTNIEKRCR |
| SEQ ID NO: 21 | — | Mutant MCa G25A | GDCLPHLKLCKENKDCCSKKCKRRATNIEKRCR |
| SEQ ID NO: 22 | — | Mutant MCa N27A | GDCLPHLKLCKENKDCCSKKCKRRGTAIEKRCR |
| SEQ ID NO: 23 | — | Mutant MCa E29A | LPHLKLCKENKDCCSKKCKRRGTNIAKRCR |
| SEQ ID NO: 24 | — | Mca/IpTxa chimera | GDCLPHLKRCKADNDCCSKKGKRAGTNIEKRCR |
| SEQ ID NO: 25 | — | Mca/lOpi chimera | GDCLPHLKRCKENNDCCSKKCKRAGTNIEKRCR |
| SEQ ID NO: 26 | — | DNA compaction peptide | CWCK$_{15}$CK |

TABLE I-continued sequence listing

| Identifier number | NCBI accession number | Peptide | Sequence |
|---|---|---|---|
| SEQ ID NO: 27 | — | DNA compaction peptide | CW(CK$_3$)$_4$CK |
| SEQ ID NO: 28 | — | DNA compaction peptide | CWK$_5$CK$_5$CK$_5$C |
| SEQ ID NO: 29 | — | Plant ICK peptide | SGSDGGVCPKILKKCRRDSDCPGACICRGNGYCG |

[1]Toxin of *Scorpio maurus palmatus*;
[2]Toxin of *Pandinus imperator*;
3 and 4: toxin of *Opistophthalmus carinatus*

EXAMPLE 1

Analysis of the Cell Penetration of Complexes of Labeled Streptavidin with Biotinylated Maurocalcine or a Biotinylated Derived Peptide According to the Invention 1) Materials and Methods
a) Peptide Synthesis Maurocalcine, the maurocalcine-derived peptides according to the present invention and their biotinylated derivatives were prepared by solid-phase peptide synthesis (Merrifield, Science, 1986, 232, 341-347), using an automatic synthesizer (model 433A, APPLIED BIOSYSTEMS). The N-α-Fmoc-L-Lys (biotin)-OH was provided by NEOSYSTEM (SNPE group). The N-α-Fmoc-L amino acid derivatives, the 4-hydroxymethylphenyloxy resin and the reagents used for the peptide synthesis were provided by PERKIN ELMER LIFE SCIENCES. The peptide chains were assembled sequentially on 0.25 meq of hydroxymethylphenyloxy resin (1% of crosslinking; 0.89 meq of amino group/g), using 1 mmol of N-α-Fmoc-L amino acid derivatives. The protective groups for the side chains are as follows: trityl for the cysteine and asparagine residues; tert-butyl for the serine, threonine, glutamic acid and aspartic acid residues; pentamethylchromane for the arginine residues, and tert-butyloxycarbonyl for the lysine residues.

The N-α-amino groups were deprotected by treatment with piperidine/N-methylpyrrolidone (18 and 20% v/v) for 3 and 8 minutes, respectively. The Fmoc amino acid derivatives were coupled (20 min), like their hydroxybenzotriazole active esters, in N-methylpyrrolidone (in 4-fold excess). After the assembly of the peptide chain, the resin containing the peptide (approximately 1.8 mg) was treated for 2 to 3 hours at ambient temperature, with continuous agitation, with a mixture of trifluoroacetic acid/H$_2$O/thioanisol/ethanedithiol (88/5/5/2, v/v) in the presence of phenol crystals (2.25 g). The peptide mixture was then filtered, and the filtrate was precipitated by addition of cold butyl methyl ether. The crude peptide was pelleted by centrifugation (3000 g for 10 min), and the supernatant was eliminated. The reduced peptide was then dissolved in 200 mM Tris-HCl buffer, pH 8.3, at a final concentration of 2.5 mM and mixed, in the open air, for 50 to 72 h, at ambient temperature, in order to allow the oxidation and folding of said peptide.

The products were then purified to homogeneity, through a first reverse-phase high pressure liquid chromatography step (HPLC; C18 Aquapore ODS column, 20 μm, 250×10 mm, Perkin Elmer Life Sciences), by means of a linear gradient of 60 min of trifluoroacetic acid (0.08% v/v), 0 to 30% of acetonitrile in 0.1% (v/v) of trifluoroacetic acid in H$_2$O, at a flow rate of 6 ml/min (λ=230 nm). A second step consisting of purification of the maurocalcine, of the maurocalcine-derived peptides according to the invention, and of their biotinylated derivatives was carried out by ion exchange chromatography, on a carboxymethylcellulose matrix, using 10 mM (buffer A) and 590 mM (buffer B) phosphate buffers, pH 9.0 (linear gradient of 0 to 60% of buffer B at a flow rate of 1 ml/min, for 1 hour). The homogeneity and the identity of the maurocalcine, of the maurocalcine-derived peptides according to the present invention and of their biotinylated derivatives was determined by: (i) C18 analytical reverse-phase high pressure liquid chromatography (C18 Li-Chrospher, 5 μm, 4×20 mm, Merck), using a linear gradient of 60 min of 0.08% v/v trifluoroacetic acid/0-60% of acetonitrile in 0.1% v/v of trifluoroacetic acid/H$_2$O, at a flow rate of 1 ml/min; (ii) amino acid analysis by acidolysis (6N HCl/2% (w/v) phenol, 20 h, at 118° C., under nitrogen) and (iii) determination of mass by mass spectrometry (MALDI).

b) Formation of Complexes with Streptavidin Coupled to Cyanin 3

Soluble streptavidin-cyanin 3 and streptavidin-cyanin 5 (Strept-Cy[3] and Strept-Cy[5], AMERSHAM) were mixed with 4 molar equivalents of biotinylated maurocalcine (1 mM) or biotinylated maurocalcine-derived peptide, in phosphate buffer (PBS, in mM: 136 NaCl, 1.47 Na$_2$HPO$_4$, 2.6 KCl, 1 CaCl$_2$, 0.5 MgCl$_2$, pH 7.2), for 2 hours at 37° C. and in the dark.

c) Cell Cultures

The L6 rat myogenic cell line (clone C5, EACC) is cultured in DMEM medium supplemented with 15% fetal bovine serum (LIFE TECHNOLOGIES) and 1% penicillin-streptomycin (Invitrogen).

Differentiation of the L6 line was induced by replacing the culture medium with differentiation medium (DMEM+5% horse serum), when the cells become confluent.

Hippocampal CA1 region neurons are prepared from newborn mouse hippocampus (1 to 2 days post-partum), dissected, freed of the meninges and placed in HBSS buffer (INVITROGEN). They are then incubated in dissociation medium (HBSS, 1% penicillin/streptomycin (GIBCO), 2000 IU/ml DNase and 1% (w/v) trypsin/EDTA), for 7 min at 37° C. After sedimentation, the supernatant is removed and the tissue is washed with HBSS medium containing 1% penicillin/streptomycin. The tissue is triturated gently in HBSS medium, 1% penicillin/streptomycin, 10% fetal bovine serum, 2000 IU/ml DNase I, using a plastic pipette, until a homogeneous suspension is obtained. After centrifugation at 100 g for 1 min, the cell pellet is resuspended in Neurobasal/B27 medium (GIBCO) containing 0.5 mM of L-glutamine and 1% of penicillin/streptomycin. The cell cultures are seeded, at a density of $10^5$ cells/cm², into culture dishes pre-treated with 20 μg/ml of poly-L-lysine, for 2 hours at 37° C. After 2 days of culture, cytosine arabinoside (3 μM) is added to the cultures in order to limit the proliferation of non-neuronal cells, and 24 hours later, half the medium is changed. The culture medium is then changed every 2 days.

The human embryonic kidney cells (HEK 293 line, ATCC) are divided before confluence, by treatment with trypsin (1%), and are maintained in DMEM medium (INVITROGEN) containing 10% of inactivated fetal calf serum (INVITROGEN) and 1% of penicillin/streptomycin (INVITROGEN), in a $CO_2$ incubator (5%). The culture medium is changed every 2 days.

d) Immunocytochemistry $d_1$) Fixed Cells

The cells were incubated with maurocalcine and the derived peptides, biotinylated and complexed with streptavidin-cyanin 3 or with streptavidin-cyanin 5, at the final concentration of 100 nM in PBS, in the dark and at ambient temperature, for 30 minutes to 1 hour. After 3 washes in PBS, the cells are fixed at ambient temperature, in a paraformaldehyde solution (4%), for 10 min, in the dark, washed in PBS and incubated for one hour with FITC-conjugated concanavalin (MOLECULAR PROBES, 5 μg/ml) in order to label the plasma membrane, and TO-PRO-3 iodide (MOLECULAR PROBES, 1 μM) in order to label the nucleus. In order to label the cytoskeleton, the cells were fixed and permeabilized with ice-cold methanol, for 10 min, washed twice in PBS and incubated with a mouse anti-alpha-tubulin antibody (1:1000, SIGMA), for 2 hours. After two washes in PBS, the cells were incubated for one hour with an anti-mouse IgG secondary antibody conjugated to Alexa 488 (1:1000, MOLECULAR PROBES). The cultures were then mounted in Vectashield mounting medium (VECTOR LABORATORIES). Preparations were observed by laser scanning confocal microscopy, using a Leica TCS-SP2 control system. The Alexa-488 and Cy3 or propidium iodide (PI) fluorescences were excited sequentially and then recorded. The Cy3 fluorescence was excited using a 543 nm helium-neon laser beam and the fluorescence emission was recorded between 554 nm and 625 nm. The images were introduced into Adobe Photoshop 7.0.

$d_2$) Live Cells

The live cells were incubated with maurocalcine and the derived peptides, biotinylated and complexed with streptavidin-cyanin 3, at the final concentration of 100 nM in PBS, at ambient temperature in freshly changed culture medium, on the platform of an upright microscope (Nikon Eclipse 600 FN, equipped with a water-immersion objective (×40); aperture 0.8) and a confocal head (Nikon PCM 2000), or else with a Leica TCS-SP2 microscope, equipped with an objective (×100), according to the "XYZt" mode.

The penetration kinetics of the maurocalcine and of the derived peptides, biotinylated in complex with streptavidin-Cy3, was initiated by injecting 100 nM of the complex into the culture medium. The Cy3 fluorescence was excited by means of a 543 nm wavelength of an argon laser. The light emission was filtered (595±35 nm filter). The images were recorded and analyzed using the EZ2000 software (Nikon).

The quantitative analysis of the relative fluorescence was carried out on the overall signal of all the cells, using appropriate software (Leica).

e) Flow Cytometry

The cells are incubated with maurocalcine and the derived peptides, biotinylated and complexed with streptavidin-cyanin 5 ($MCa_b$-Strept-$Cy^5$ complexes), at the final concentration of 100 nM in PBS, in the dark and at ambient temperature for 1 hour. After 2 washes in PBS (PBS, in mM: 0.15 NaCl, 6.84 $Na_2HPO_4$, 3.16 $NaH_2PO_4$, pH 7.2), and the cells were treated with trypsin (1 mg/ml, INVITROGEN), for 10 min at 37° C., in order to remove the extracellular complexes and the plasma-membrane-bound complexes. After the incubation with trypsin, the cell suspension was centrifuged at 500 g and the cells were resuspended in PBS containing 1 μg/ml of propidium iodide (SIGMA). For the experiments which do not include a propidium iodide treatment step (dose-response curve), the $MCa_b$-Strept-$Cy^3$ complex is used in place of the $MCa_b$-Strept-$Cy^5$ complex. The analysis was carried out on live cells, using a flow cytometer (FACScalibur, BECTON DICKINSON). The data were recorded and analyzed using appropriate software (CellQuest, BD BIOSCIENCES). The live cells were sorted according to their size and their granulosity (forward/side scattering), over a total of 10 000 events.

2) Results a) Penetration Analysis

Maurocalcine variants (SEQ ID Nos. 2 to 8 and 12 to 23), and also two chimeras of maurocalcine with either imperatoxin (SEQ ID No. 24) or opicalcine (SEQ ID No. 25), were synthesized:

```
GDCLPHLKRCKADNDCCSKKCKRAGTNIEKRCR   (SEQ ID No. 24)
and
GDCLPHLKRCKENNDCCSKKCKRAGTNIEKRCR.  (SEQ ID No. 25)
```

Each of the chimeras also comprises the substitution, to alanine, of the arginine at position 24 of the maurocalcine sequence (R24A) or at position 15 ($X_{15}$=A) of formula (I).

The ability of the maurocalcine-derived peptides according to the present invention to transduce various cell types and to transport macromolecules is studied using complexes of biotinylated peptides with cyanin-3-coupled streptavidin. The biotinylated maurocalcine-streptavidin-Cy3 complexes ($MCa_b$/Strept-Cy3) serves as a control.

The primary rat hippocampal neurons and the cells of the HEK293 line and the L6 line (before and after differentiation) are incubated for 30 min at ambient temperature, with 100 nM or 333 nM of maurocalcine-derived peptide, biotinylated and complexed with streptavidin-Cy3, or else 100 nM or 333 nM of $MCa_b$/Strept-Cy3, as a control. The cells are fixed and the fluorescence is observed by confocal microscopy.

Figure 2:
FIG. 2 shows that the $MCa_b$/Strept-Cy3 complex effectively transduces many different cell cultures. Cultures of CA1 hippocampal neurons, of HEK293 cells and of undifferentiated L6 cells were incubated for 30 min with 100 nM of biotinylated maurocalcine, complexed with cyanin-3-labeled streptavidin ($MCa_b$/Strept-Cy3), and the cells were then fixed and analyzed by confocal microscopy. Differentiated L6 cells were treated in a similar manner. The panels that are four times smaller represent the control experiments, in which the cells were treated with a mixture of nonbiotinylated MCa and of Strept-Cy3.

The results obtained with the $MCa_b$/Strept-Cy3 complexes (FIG. 2) validated the experimental approach used to analyze the cell penetration of the maurocalcine-derived peptides, biotinylated and complexed with streptavidin-Cy3. In fact, strong uniform labeling of the plasma membrane and of the cytoplasm of all the cells is observed, whereas the nucleus is weakly labeled. On the other hand, the cells incubated in the presence of 100 nM of nonbiotinylated maurocalcine or of an equivalent concentration of Strept-Cy3 do not show any labeling, demonstrating that Strept-Cy3 alone is not capable of transducing the cells. The association of Strept-Cy3 with biotinylated maurocalcine is necessary in order for the fluorescent complex to enter the cells, demonstrating the active role of maurocalcine in this process. These results demonstrate that maurocalcine does not behave solely as a cell-penetrating peptide (CPP), but that, like the other CPPs, it is also capable of transporting high-molecular-weight proteins into cells (streptavidin is 14.6 times larger than maurocalcine).

Figure 3:
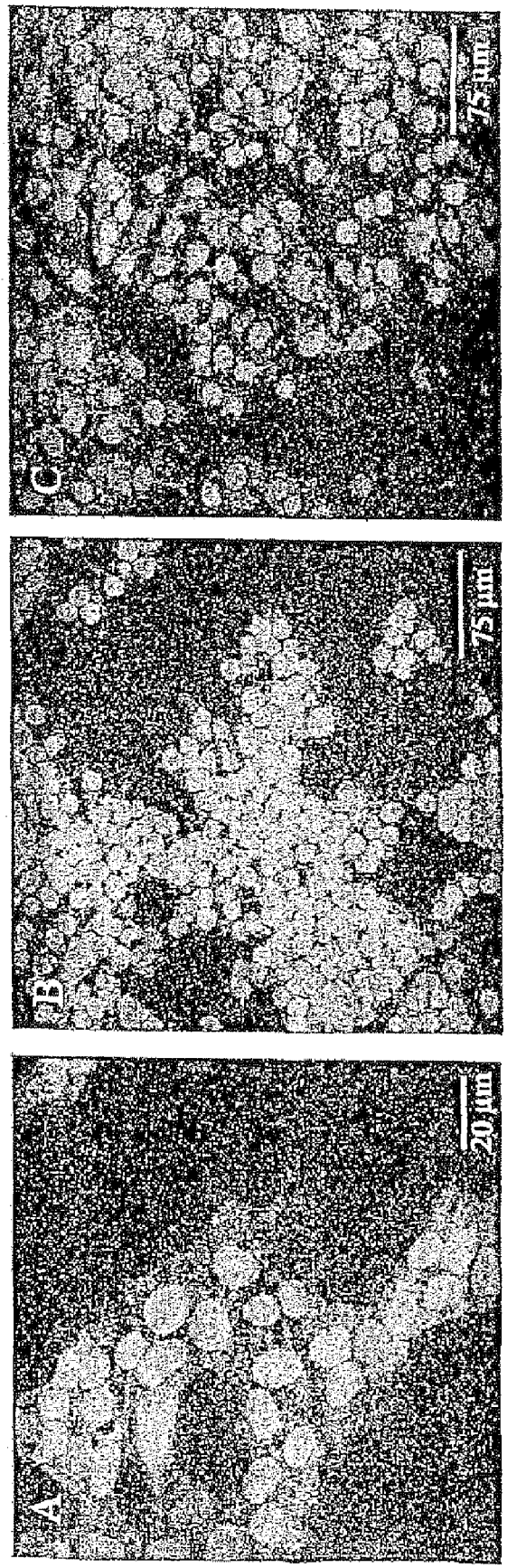
FIG. 3 shows that the complexes of the biotinylated maurocalcine variants R24A and L7A, with the cyanin-labeled streptavidin, effectively transduce cell cultures. HEK293 cell cultures were incubated for 30 min with 333 nM of variant R24A or L7A or of maurocalcine, biotinylated and complexed with cyanin-3-labeled streptavidin ($MCa_b$/Strept-Cy3), and the cells were then fixed and analyzed by confocal microscopy.

The maurocalcine variants are also capable of penetrating into the cells and transporting substances into these cells (FIG. 3).

The quantitative analysis (FIGS. 4 and 5) shows that the penetration is nonsaturable, which is coherent with a mechanism of diffusion of maurocalcine and of the derived peptides. The penetration of the maurocalcine and of the derived peptides is efficient, since they penetrate into the cells at concentrations as low as 10 nM. Certain variants (L7A, for example; FIG. 5) have a significantly increased penetrating activity compared with maurocalcine (factor of 5 for the L7A variant), whereas others have a penetration that is comparable to, or even slightly less than, maurocalcine (R24A variant, for example; FIG. 5).

b) Penetration Kinetics $b_1$) Analysis Over a Period of One Hour

Figure 6:
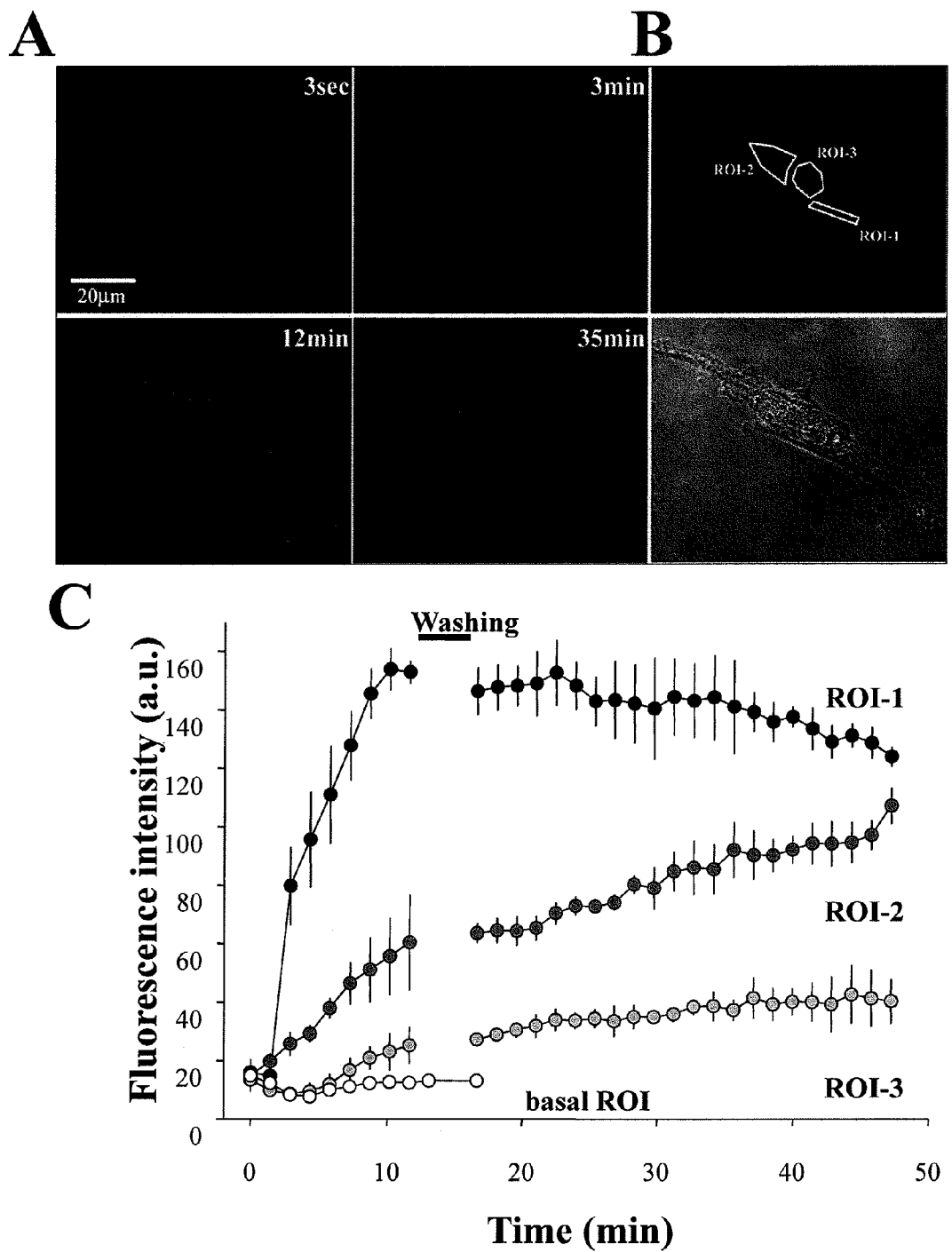
FIG. 6 represents the kinetics of transduction of the $MCa_b$/Strept-Cy3 complex in undifferentiated L6 cells, over a period of one hour. (A) Confocal image of the Cy3 fluorescence of an undifferentiated L6 cell, 3 sec, 3 min and 12 min after the addition of 100 nM of $MCa_b$/Strept-Cy3 and 23 min after washing of the complex (35 min in total). (B) Position of the various regions of interest (ROI) on the image of light transmitted by the cell (differential interference contrast, upper panel) and corresponding position of the confocal image of the Cy3 fluorescence. (C) Change in Cy3 fluorescence intensity normalized with respect to the unit of surface area of the regions of interest, as a function of time, in the various compartments of the L6 cells. The $MCa_b$/Strept-Cy3 complex was applied at the concentration of 100 nM in the medium at t=0, then at t=12 min, and it was removed from the medium by washing for 5 min. The "basal ROI" corresponds to the fluorescence intensity of the extracellular medium. The values represent the means±standard deviation of 5 different cells. Similar results were observed in the three different cell preparations.

The confocal microscopy analysis of the fluorescence kinetics of undifferentiated live L6 cells, over a period of one hour, shows that the labeling appears starting from 3 min after the addition of $MCa_b$/Strept-Cy3 to the extracellular medium (100 nM) (FIG. 6A). Three regions of interest, corresponding respectively to the plasma membrane (ROI-1), to the cytoplasm (ROI-2) and to the nucleus (ROI-3), were defined. The positioning of the various regions of interest was facilitated by analysis of the image of the light transmitted by the observed cell (FIG. 6B). The change in fluorescence intensity in the various ROIs was analyzed as a function of time (FIG. 6C).

At the beginning of the application of 100 nM of $MCa_b$/Strept-Cy3 complex to the medium, the fluorescence intensity increases in all the compartments, but with different speeds. The fastest and strongest change occurs in the plasma membrane (ROI-1), with a peak at 10 min. A slower, but considerable, increase in fluorescence is also observed in the cytoplasmic compartment (ROI-2), whereas a much smaller increase, but which is greater than the background noise, is observed in the nucleus (ROI-3).

The speed and the relative intensity at which the fluorescence increases in each compartment are coherent with the direction of progression of the $MCa_b$/Strept-Cy3 complexes in the cell, i.e.: from the extracellular space to the plasma membrane, from the plasma membrane to the cytoplasm, and then from the cytoplasm to the nucleus. The signal recorded in the ROI-1 compartment is probably overestimated, due to contamination by the fluorescence of the probe located in the cytoplasm. On the other hand, the relative intensity of the cytoplasmic fluorescence should be more precise. In addition, the passage from the cytoplasm to the nucleus is very small, indicating that this transition is much less favored than the other two. The change in fluorescence was also followed after elimination of the $MCa_b$/Strept-Cy3 complexes by washing: 12 min of incubation in the presence of $MCa_b$/Strept-Cy3 complex and 5 min of washing (FIG. 6C).

Under these conditions, the fluorescence intensity of the ROI-1 region decreases, whereas that of ROI-2 increases and that of ROI-3 remains constant. The increase in fluorescence in the cytoplasmic compartment is due to a constant transfer of complexes, from the plasma membrane to the cytoplasm.

$b_2$) Analysis Over a Period of 24 Hours

Figure 7:
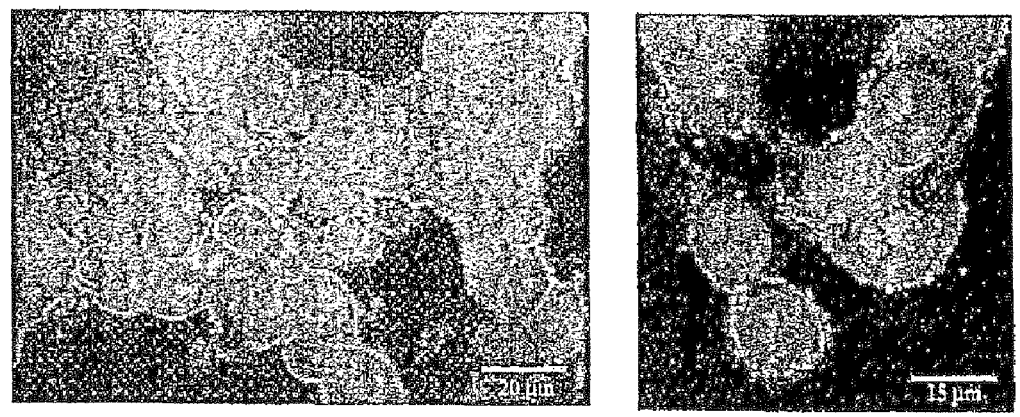
FIG. 7 illustrates the subcellular localization of the $MCa_b$/Strept-Cy5, analyzed by confocol microscopy immunofluorescence and compared with the localization of concanavalin A (A), alpha-tubulin (B), and as a function of time (C). A. Subcellular localization of the $MCa_b$-Strept-Cy5 complexes in the HEK293 cells, by comparison with a plasma membrane label. The cells are incubated for one hour in the presence of $MCa_b$-Strept-Cy5 complexes (333 nM). The plasma membrane is labeled with concanavalin and the nuclei with propidium iodide. The images represent a single confocal plane. B. As in (A), but by comparison with a cytoskeletal label (anti-alpha-tubulin antibody). C. Modifications of the cellular distribution of the $MCa_b$-Strept-Cy5 complexes after cellular translocation. Cy3 ($MCa_b$-Strept-Cy3 complexes) and To-PRO (nuclei) confocal fluorescence images of HEK293 cells incubated with 333 nM of complexes, for 2 hours, 4 hours and 24 hours. Gradual labeling of the nuclei by the $MCa_b$-Strept-Cy5 complexes is observed.
Figure 7:
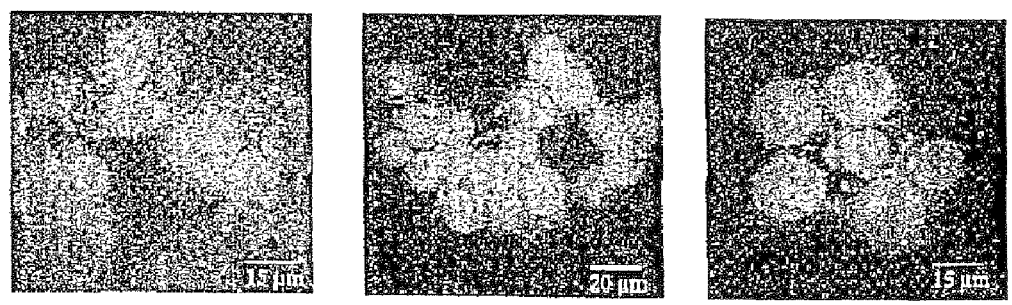

The cellular distribution of the $MCa_b$/Strept-Cy5 complexes in HEK 293 cells was then analyzed by confocal microscopy, after one hour of incubation with 333 nM of complexes (FIG. 7A). The labeling of the HEK 293 cell surface was carried out using concanavalin A, whereas the nuclei of the cells were labeled with propidium iodide (FIG. 7A). Comparison of these labelings with that of the $MCa_b$/Strept-Cy5 complexes clearly demonstrates the presence of the complexes, both at the plasma membrane and in the cytoplasm. The distribution of the $MCa_b$/Strept-Cy5 complexes was also compared with that of alpha-tubulin, which is a cytoskeletal label (FIG. 7B). An absence of colocalization is clearly demonstrated, suggesting that the cytoskeleton is not involved in the distribution of the complexes. Next, the change in cellular distribution of the $MCa_b$/Strept-Cy3 complexes was followed over time. After 2 hours of incubation, the complex is mainly present in the cytoplasm. Between 4 hours and 24 hours of incubation, it is mainly perinuclear and colocalizes with the nucleus. The biological target of maurocalcine is the RyR receptor, which is strictly located in the cytoplasm. The localization of $MCa_b$/Strept-Cy3 in the nucleus cannot therefore result from its binding to RyR1.

EXAMPLE 2

Figure 8:
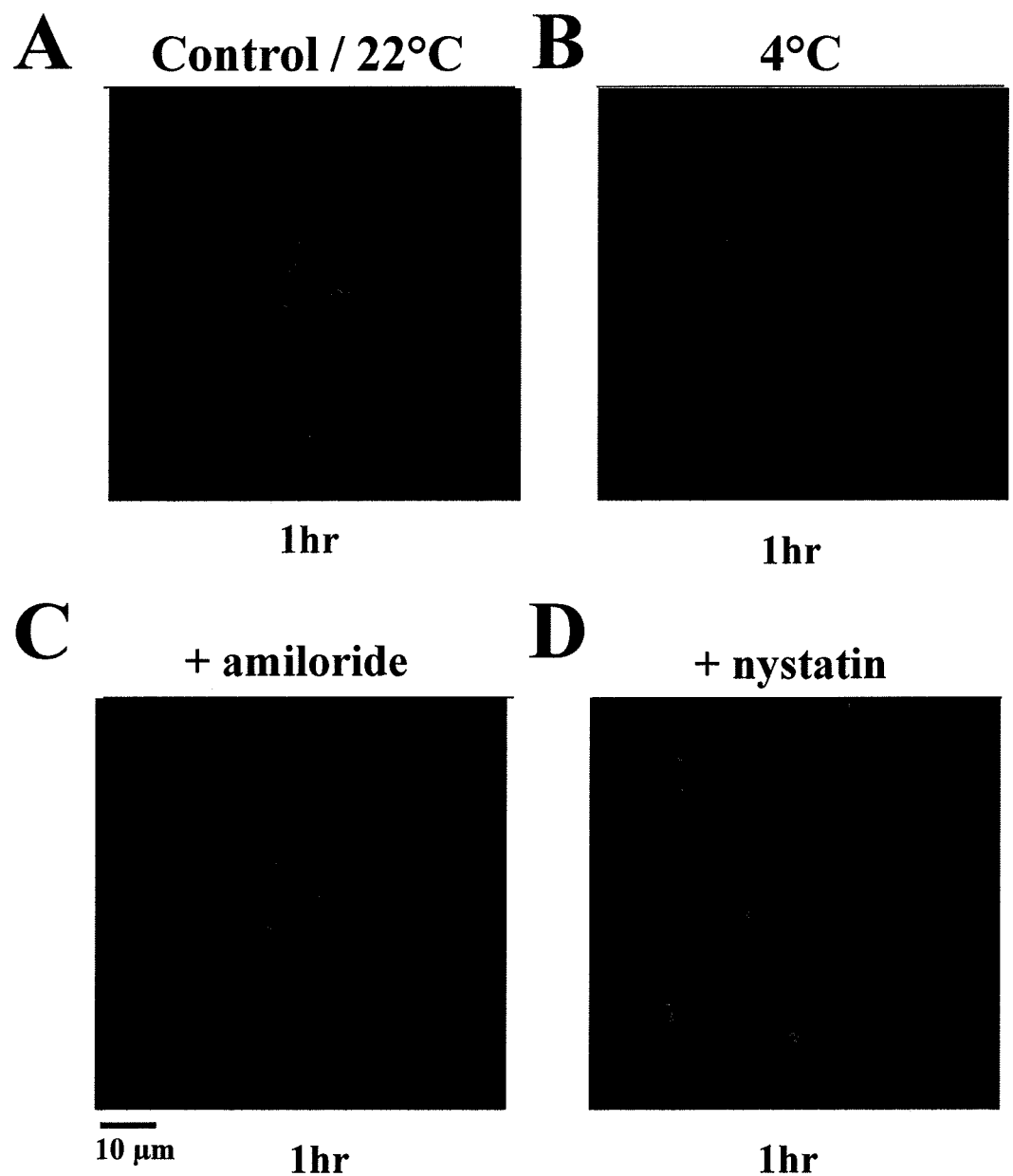
FIG. 8 shows that the entry of the $MCa_b$/Strept-Cy3 complex into the cell does not require energy. (A) Control condition for the entry of the $MCa_b$/Strept-Cy3 complex into the HEK293 cells. The cells are incubated in the presence of 100 nM of complex, for 1 h at 22° C. The cells were fixed and the images were acquired by confocal microscopy. (B). Effect of the temperature on the penetration of the $MCa_b$/Strept-Cy3 complex. The cells were incubated and observed under the same experimental conditions as at 22° C. (C) Effect of nystatin (50 µM) on the penetration of the $MCa_b$/Strept-Cy3 complex into the HEK293 cells. Nystatin is a pinocytosis inhibitor. The conditions are identical to those used in (A). (D) Effect of amiloride (3 mM) on the penetration of the $MCa_b$/Strept-Cy3 complex into the HEK293 cells. Amiloride is a caveolar endocytosis inhibitor. The conditions are identical to those in (A)

Analysis of the Mechanisms Involved in the Cellular Penetration of Maurocalcine and of the Derived Peptides a) The Penetration of Maurocalcine and of the Derived Peptides is Energy-Independent and Insensitive to Endocytosis Inhibitors The possible contribution of an energy-dependent process in the entry of the $MCa_b$/Strept-Cy3 complexes into cells was studied (FIG. 8). The effect of a decrease in temperature on the entry of the $MCa_b$/Strept-Cy3 complexes shows that they still penetrate into the cells at 4° C. (FIG. 8B). At this temperature, the complex labels the membrane and the cytoplasm in a similar manner. The effect of pinocytosis/endocytosis inhibitors was also tested. Both amiloride (3 mM, FIG. 8C) and nystatin (50 µM, FIG. 8D) have no effect on the entry of the complex into the cells or on its relative distribution on the plasma membrane and in the cytoplasm, further confirming that the principle mechanism of entry of maurocalcine into the cell is not energy-dependent.

b) Maurocalcine and the Derived Peptides Diffuse Through Membranes $b_1$) Experimental Protocol The analysis is carried out as described in Example 1. For the heparin treatment experiments, the complexes were prepared in a heparin solution (bovine intestine heparin, sodium salt, SIGMA) and the cells were washed twice with the heparin solution, before and after incubation with the complexes prepared in the same heparin solution.

$b_2$) Results

The cellular penetration was analyzed by flow cytometry, on cells incubated with the $MCa_b$/Strept-Cy3 complexes, and then treated with trypsin, so as to remove the complexes bound to the plasma membrane by means of lipids, specific receptors or heparan sulfate glycosaminoglycan (HPSG). It has been shown that this method makes it possible to effectively study the entry of penetrating peptides into cells (Richard et al., J. Biol. Chem., 2003, 278, 585-590).

Figure 9:
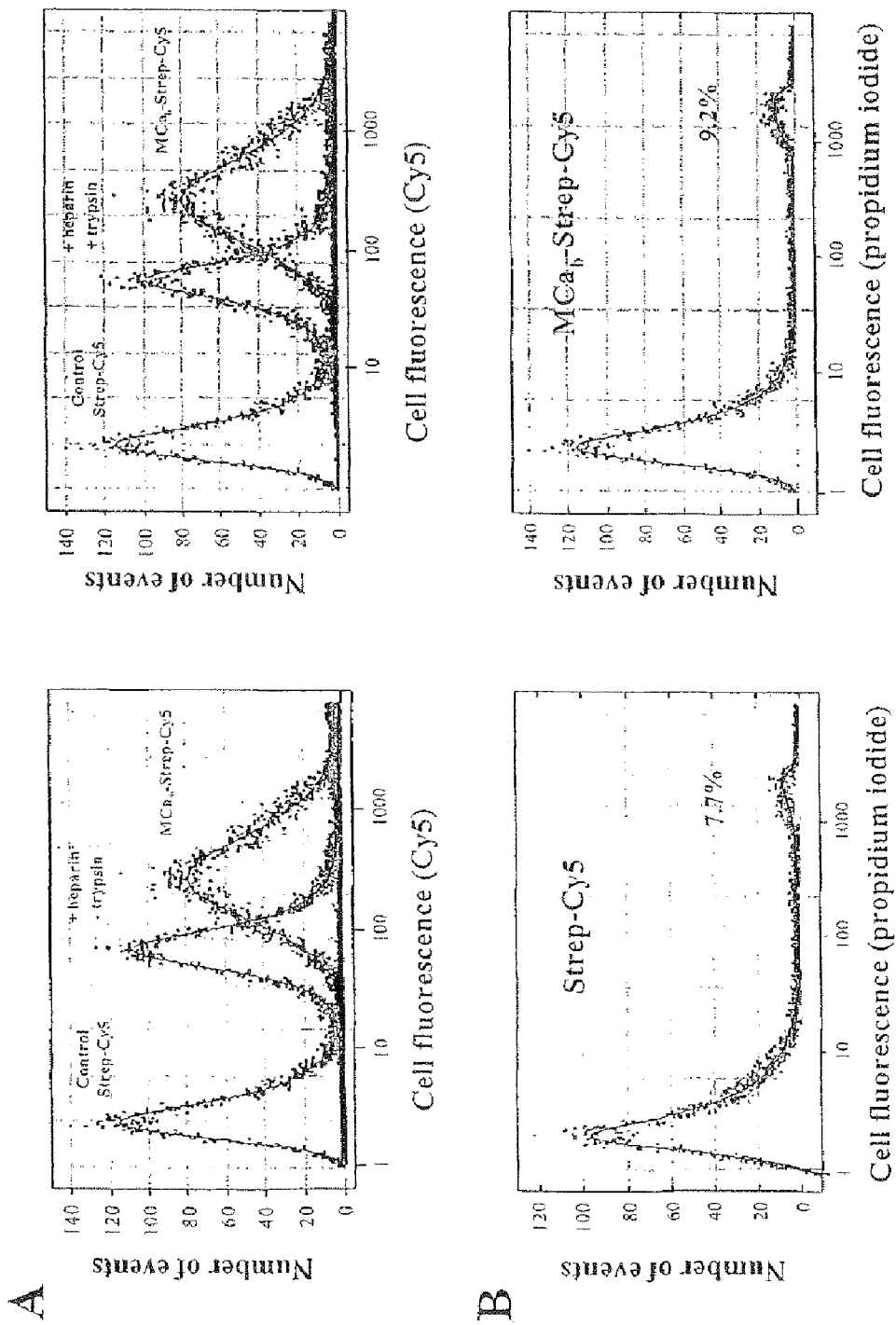
FIG. 9 illustrates the flow cytometry analysis of the effect of treatment with heparin and/or with trypsin on the cellular penetration of the $MCa_b$-Strept-Cy5 complexes (A) and the cellular toxicity of the complexes (B). (A) The incubation of the cells and of the $MCa_b$-Strept-Cy5 complexes with 10 µg/ml of heparin reduces the penetration of the complex (left panel). The mean fluorescence value of Cy5 is 307 without treatment, whereas, in the presence of heparin, it drops to 78. The treatment of the cells and of the $MCa_b$-Strept-Cy5 complexes with 10 µg/ml of heparin, combined with the treatment of the cells with trypsin (1 mg/ml), further decreases the mean fluorescence to the value of 64. The control fluorescence, after treatment with Strept-Cy5 alone reaches the value of 3.1 and is not influenced by the trypsin or heparin treatment. The penetration of the $MCa_b$-Strept-Cy5 complexes is tested at the concentration of 1 µM. (B) The cellular toxicity of 1 µM of Strept-Cy5 or $MCa_b$-Strept-Cy5 complex, analyzed by cellular incorporation of propidium iodide. The proportion of cells labeled with propidium iodide is indicated as percentages.

FIG. 9A shows that the heparin reduces the penetration of maurocalcine into the cells, by hindering its interaction with heparan sulfate glycosaminoglycan or by impairing its properties of interaction with the negatively charged lipids, by binding to its basic face. FIG. 9A also shows that the fraction of $MCa_b$/Strept-Cy3 which is associated at the outer surface of the plasma membrane, in particular by binding to the heparan sulfate, is minimal since the effect of the trypsin treatment on the cellular penetration is weak (compare left panel and right panel). These results indicate that the penetration of maurocalcine and of the derived peptides does not require a transporter or heparan sulfate and does not therefore involve a mechanism of endocytosis.

Figure 4:
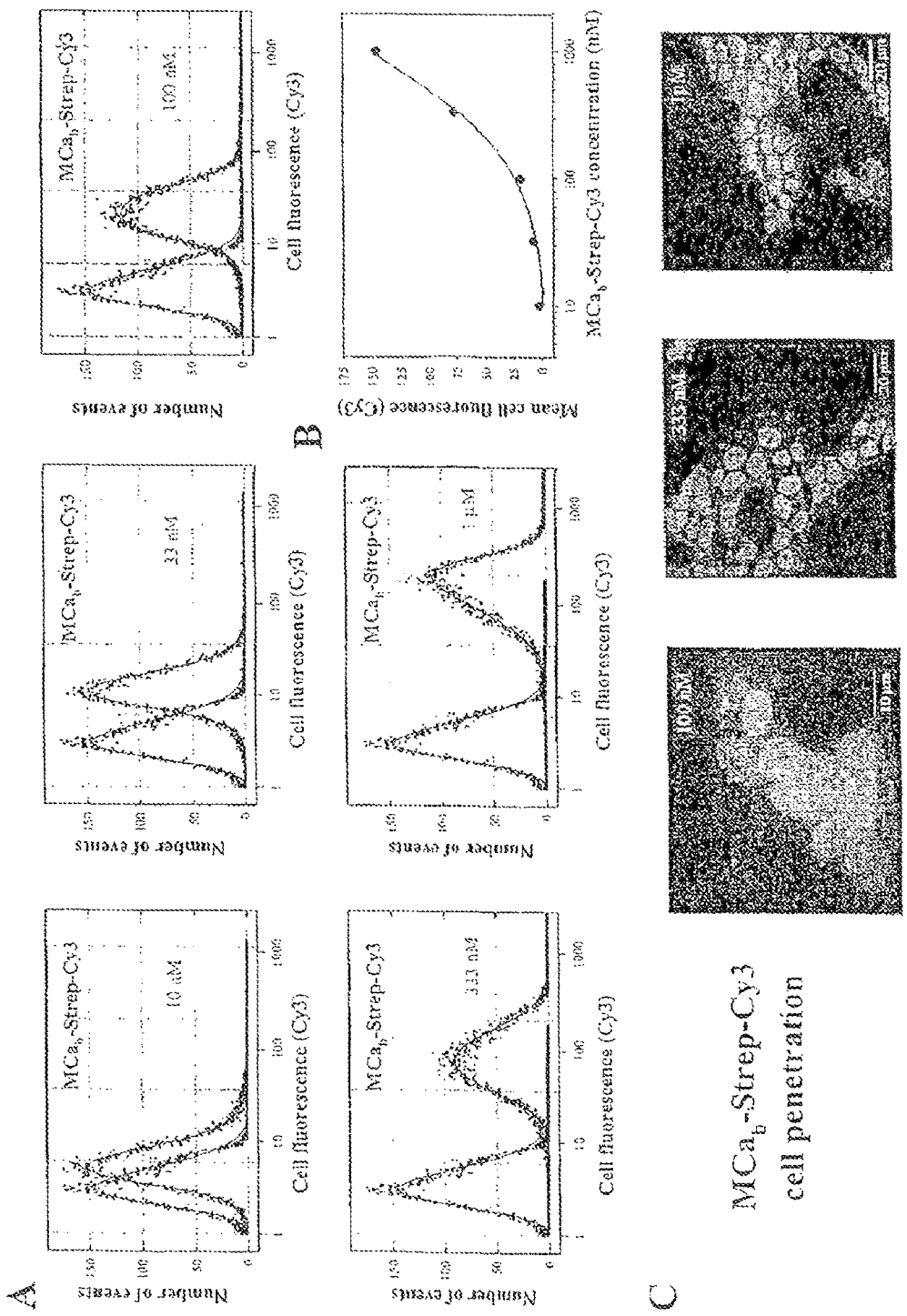
FIG. 4 shows that the penetration of the $MCa_b$/Strept-Cy3 complexes is dose-dependent. A. Flow cytometry analysis of the penetration of the $Mca_b$/Strept-Cy3 complexes at the concentrations indicated (10 nM, 33 nM, 100 nM, 333 nM and 1 μM). The cells were treated with trypsin (1 mg/ml), before the flow cytometry analysis. B. Mean cell fluorescence, as a function of the concentration of $MCa_b$/Strept-Cy3 complexes. The values correspond to the following equation $y = y_0 + aX(1-\exp(-b \times x))$ in which $y_0 = -3.8$, $a = 199$ and $b = 1.5 \times 10^{-3}$. C. Confocal immunofluorescence images of HEK293 cells incubated for 1 hour with various concentrations of $MCa_b$/Strept-Cy3 complexes. The nuclei are stained with To-PRO-3.
Figure 5:
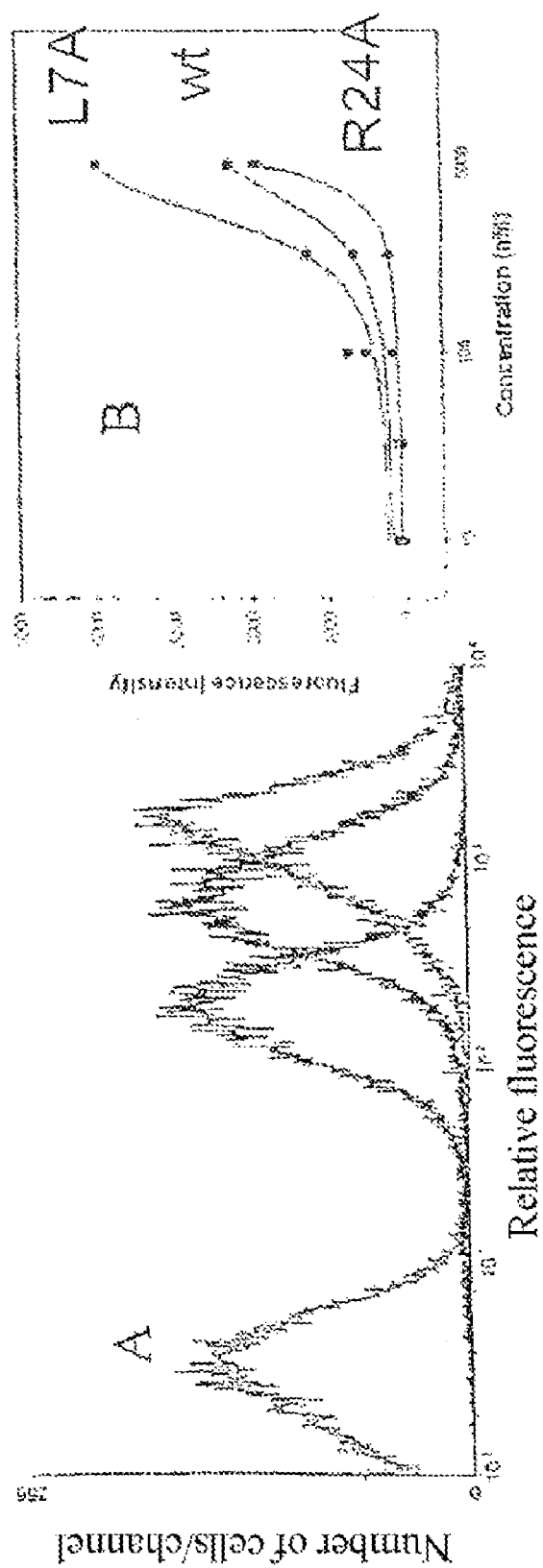
FIG. 5 shows that the penetration of the complexes of the biotinylated maurocalcine variants, with the cyanin-labeled streptavidin is dose-dependent. A. Flow cytometry analysis of the penetration of the complexes of the biotinylated variants R24A or L7A or maurocalcine, with the Strept-Cy3. The cells were treated with trypsin (1 mg/ml), before the flow cytometry analysis. B. Mean cell fluorescence, as a function of the concentration of complexes.

FIG. 4 also shows that the penetration of the MCa$_b$/Strept-Cy3 complexes cannot be saturated, which is compatible with a mechanism of diffusion of maurocalcine and of the derived peptides.

In addition, FIG. 9B shows an absence of incorporation of propidium iodide by the live cells incubated in the presence of MCa$_b$/Strept-Cy5 complex (complex concentration 1 µM); this absence signaling a notable absence of cellular toxicity of maurocalcine in the presence of streptavidin-Cy5.

c) The Penetration of Maurocalcine and of the Derived Peptides is Sensitive to the Membrane Potential c$_1$) Experimental Protocol The MCa$_b$-Strept-Cy$^5$ complexes were prepared in solutions containing various NaCl/KCl ratios (composition in mM: 145 to 5 NaCl, 5 to 145 KCl, 2.5 CaCl$_2$, 1.2 MgCl$_2$, 10 glucose, 10 HEPES, pH 7.4).

The cells were washed twice with the NaCl/KCl solution used to prepare the complexes, and then incubated with maurocalcine and the derived peptides, which are biotinylated and complexed with streptavidin-cyanin 3 (MCa$_b$-Strept-Cy$^3$ complexes), at the final concentration of 100 nM in the same NaCl/KCl solution, in the dark and at ambient temperature for 1 hour. After 2 washes in the same NaCl/KCl buffer, the cyanin 3 fluorescence was analyzed on live cells, using a flow cytometer (FACScalibur, BECTON DICKINSON). The data were recorded and analyzed using appropriate software (CellQuest, BD BIOSCIENCES). The live cells were sorted according to their size and their granulosity (forward/side scattering), over a total of 10 000 events.

c$_2$) Results

Figure 10:
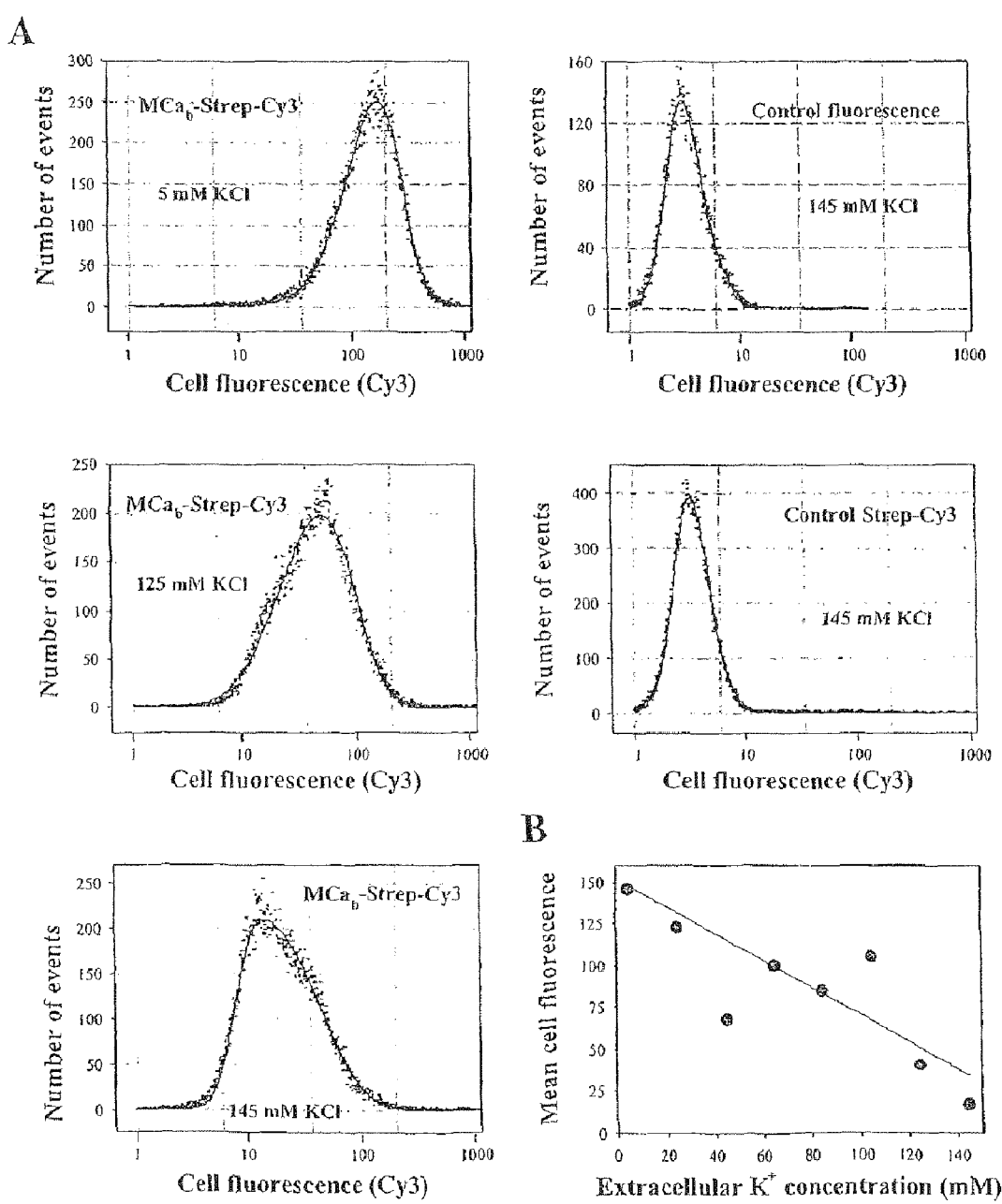
FIG. 10 illustrates the effect of increasing the extracellular concentration of K+ on the cellular penetration of the $MCa_b$-Strept-Cy3 complexes (A, B). (A) Flow cytometry analysis of the effects of increasing the concentrations of KCl on the cellular penetration of the $MCa_b$-Strept-Cy3 complexes. The right panels correspond to the controls (cell fluorescence without complex (top) and with Strept-Cy3 (bottom)), in the presence of 145 mM KCl. The KCl gradient has no effect on the values of the controls. The left panels illustrate the effect of 5 mM (top, mean fluorescence value of 145), 125 mM (middle, mean fluorescence value of 40) and 145 mM (bottom, mean fluorescence value of 17) KCl, respectively. (B) Change in mean fluorescence as a function of KCl concentration. Linear regression of the values with $y=y_0+a \times x$ with a maximum fluorescence $y_0=139.5$ and a decreasing slope $a=-0.72$.

The depolarization of the cells due to the increase in extracellular KCl concentration limits the penetration of maurocalcine by approximately 50% (FIGS. 10A and 10B). The quantitative analysis (FIG. 10B) shows that the membrane depolarization induces a linear decrease in fluorescence intensity. This result indicates that the membrane potential acts as a driving force for the penetration of the basic molecule, namely maurocalcine.

d) Interaction of Maurocalcine with Lipids d$_1$) Experimental Protocol

The disialoganglioside NeuAcα2-8NeuAca2-3Galb1-aGlcb1-Cer (GD3) and dipalmitoylphosphatidylcholine (DPPC) were provided respectively by MATREYA INC and SIGMA.

The surface pressure was measured using an automatic microtensiometer (µ THROUGH SX, KIBRON INC.). The apparatus makes it possible to record kinetics of interaction of a ligand with a monomolecular film using a series of appropriate Teflon probes. All the experiments were carried out in a controlled atmosphere at 20±1. The molecular films of the lipids indicated were deposited onto an aqueous phase of ultrapure water (800 µl), using hexane:chloroform:ethanol (11:5:4, v/v/v), as described previously (Mahfoud et al., J. Biol. Chem., 2002, 277, 11292-11296). After spreading of the film, a minimum period of elapsed time of 5 min was observed, in order to allow the solvent to evaporate off. In order to measure the interaction of MCa with the lipid monolayers, various concentrations of peptides were injected into the monomolecular film with a 10 ml Hamilton syringe and the resulting increase in pressure, produced by the incorporation of the peptide, was recorded until equilibrium was reached (maximum increase in surface pressure generally reached after an incubation of 100 to 150 min). For the dose-dependent interaction between MCa and GD3, the monomolecular films of GD3 were prepared at an initial surface pressure (p$_i$) of 10 mN·m$^{-1}$. The results were analyzed with Filmware 2.5 software (KIBRON INC.). The system for measuring the surface pressures was accurate to 0.25 mN·m$^{-1}$ under the experimental conditions.

d$_2$) Results

Figure 11:
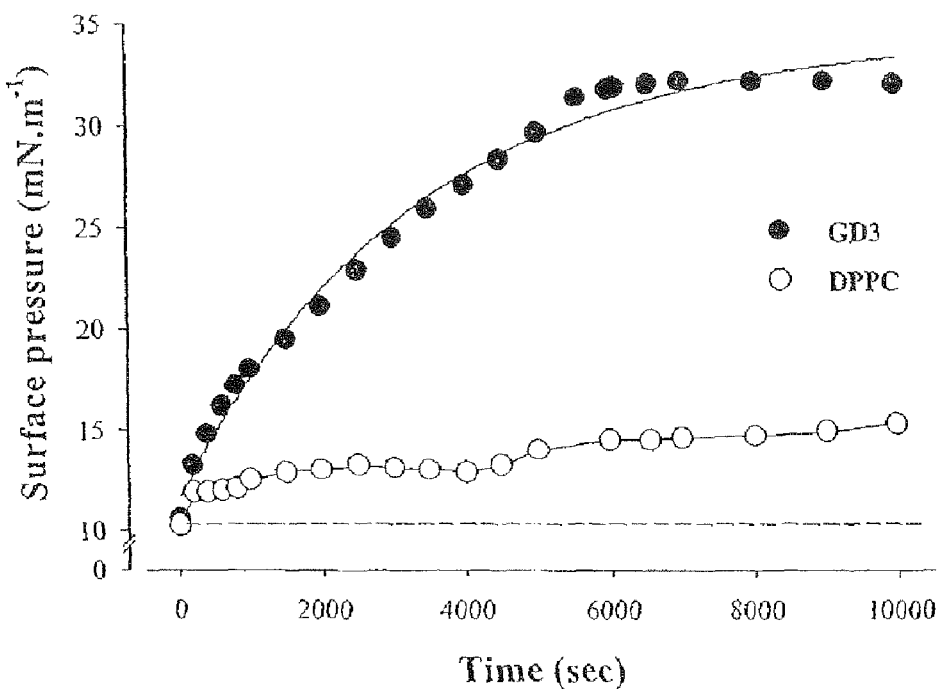
FIG. 11 represents the interaction of MCa with the membrane lipids (A, B). A. Measurement of the surface pressure of monomolecular films of GD3 and DPPC. Kinetics of surface pressure changes induced by the application of 1 µM MCa. The results illustrate the interaction of MCa with GD3, but not DPPC. The initial surface pressure was of the order of 10 $mN \cdot m^{-1}$. The results correspond to a sigmoidal increase toward a maximum, according to the equation $y=y_0+aX(1-exp(-b \times x))$ in which the initial surface pressure $y_0=11.6$ $mN \cdot m^{-1}$, the maximum increase in surface pressure $a=22.9$ $mN \cdot m^{-1}$ and the time constant for the change in surface pressure $b+3 \times 10^{-4}$ $sec^{-1}$. (B) Change in surface pressure of the GD3 films as a function of MCa concentration. The results correspond to a sigmoidal function $y=a/(1+exp(-(x-x_0)/b))$ in which the maximum increase in surface pressure $a=22.1$ $mN \cdot m^{-1}$, the slope $b=0.006$ and 50% of the maximum effect is obtained at the concentration $X_0=0.49$ µM.
Figure 11:
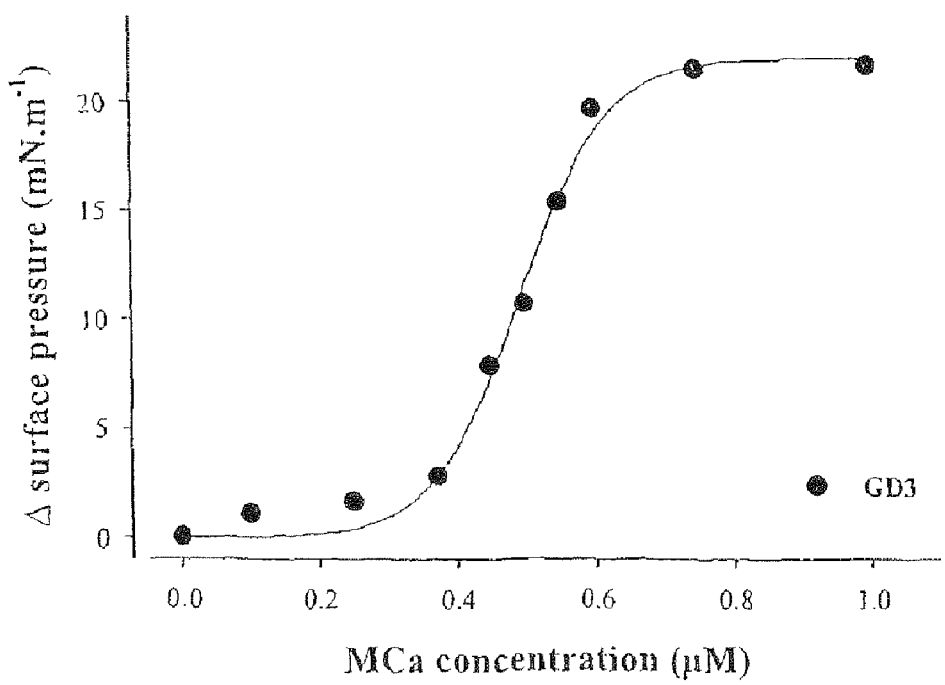

In order to determine whether maurocalcine is capable of interacting with specific membrane lipids, monomolecular films of DPPC and of GD3 ganglioside were spread at the air-water interface. Maurocalcine was then added to the aqueous phase at the concentration of 1 µM. The various in surface pressures of the film were recorded continuously, as a function of time (FIG. 11A). The results suggest that maurocalcine is capable of penetrating through the GD3 monolayer, as shown by the considerable increase in surface pressure of the GD3 film. On the other hand, maurocalcine produces no significant change in surface pressure of the DPPC film, indicating that maurocalcine does not recognize this glycerophospholipid. FIG. 11B shows that the interaction of maurocalcine with GD3 is dose-dependent. The interaction is detectable at concentrations of 100 nM of maurocalcine and reaches a maximum at 750 nM. The concentration that produces 50% of the maximum effect is 500 nM.

These results indicate that the initial site of interaction of maurocalcine (MCa) with plasma membranes is located in ganglioside-enriched domains. The representation of surface electrostatic potential shows that maurocalcine has a basic face involving G$_1$ and all the lysines and a hydrophobic face, and indicates that maurocalcine is a highly charged molecule which has a large dipolar moment (FIG. 1B). Consequently, it could be envisioned that the GD3/MCa interactions neutralize the basic face of MCa and promote the interaction of its hydrophobic face with the inner part of the membrane. GD3 could transiently translocate from the outer face of the membrane to the inner face in order to release MCa, which could then establish new electrostatic interactions with other negatively charged lipids or proteins, due to an environment richer in negative charges.

EXAMPLE 3

Analysis of the Effect of the Biotinylated MCa-Derived Peptide/Strept-Cy3 Complexes on the Biological Activity of the RyR1 Receptor 1) Materials and Methods a) Preparation of Heavy Sarcoplasmic Reticulum Vesicles The heavy sarcoplasmic reticulum vesicles are prepared according to the method of Kim et al. (J. Biol. Chem., 1983, 258, 9662-9668) modified as described in Marty et al. (J. Biol. Chem., 2000, 275, 8206-8212). The protein concentration is measured by the Biuret method.

b) Tritiated Ryanodine Binding Assay

The heavy sarcoplasmic reticulum vesicles (1 mg/ml) are incubated at 37° C. for 2 hours and 30 min, in reaction buffer comprising 5 nM [$^3$H]-ryanodine, 150 mM NaCl, 2 mM EGTA, 2 mM Ca$^{2+}$ (pCa=5) and 20 mM Hepes, pH 7.4. Maurocalcine, the maurocalcine-derived peptides and their biotinylated derivatives are added before the addition of the heavy sarcoplasmic reticulum vesicles. The [$^3$H]-ryanodine bound to the heavy sarcoplasmic reticulum vesicles is measured by filtration through Whatmann GF/B filters, followed by three washes with 5 ml of ice-cold washing buffer (150 mM NaCl, 20 mM Hepes, pH 7.4). The [$^3$H]-ryanodine retained on the filters is measured by liquid scintillation. The nonspecific binding is measured in the presence of labeled ryanodine (20 μM). The results are given in the form of means±standard deviation. Each experiment is carried out in triplicate and repeated at least twice.

c) Measurement of $Ca^{2+}$ Release

The $Ca^{2+}$ release by the heavy sarcoplasmic reticulum vesicles was measured using a $Ca^{2+}$-sensitive dye, antipyrylazo III. The absorbance was measured at 710 nm, using a diode-array spectrophotometer (MOS-200, Optical System, BIOLOGIC). The heavy sarcoplasmic reticulum vesicles (50 μg) were actively loaded with $Ca^{2+}$, at 37° C., in 2 ml of buffer containing 100 mM KCl, 7.5 mM sodium pyrophosphate, 20 mM MOPS, pH 7.0, to which 250 μM of antipyrylazo III, 1 mM ATP/$MgCl_2$, 5 mM phosphocreatine and 12 μg/ml of creatine phosphokinase had been added (Palade, J. Biol. Chem., 1987, 262, 6142-6148).

The calcium loading begins with sequential additions of 50 μM and 20 μM $CaCl_2$.

Under these loading conditions, no calcium-induced calcium release interferes with the observations. At the end of each experiment, the $Ca^{2+}$ remaining in the vesicles is measured by the addition of 4 μM of $Ca^{2+}$ ionophore, A231287 (Sigma), and the absorbance signal is calibrated by means of two consecutive additions of 20 μM $CaCl_2$.

2) Results

Figure 12:
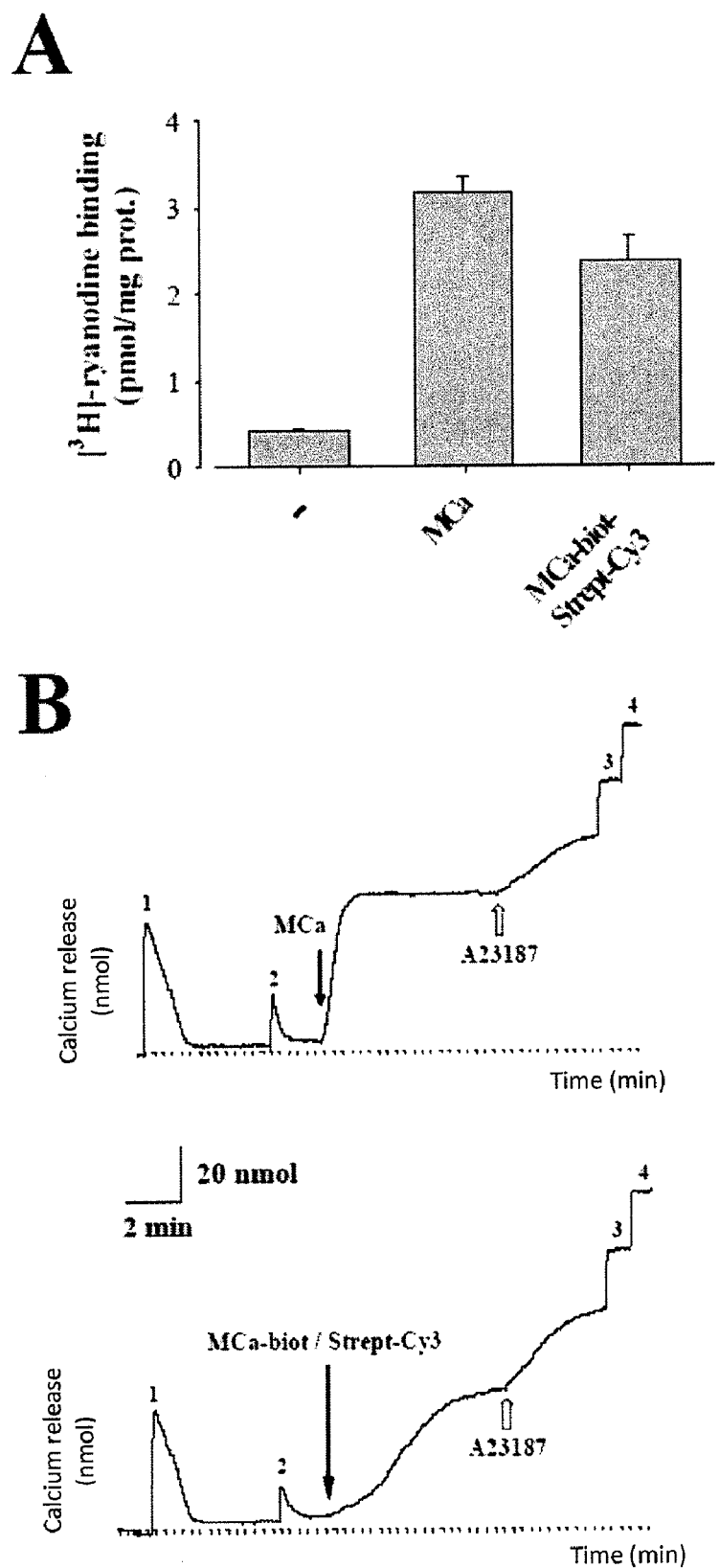
FIG. 12 illustrates the effect of the $MCa_b$/Strept-Cy3 complex on the RyR1 receptor. (A) Stimulation of the binding of [$^3$H]-ryanodine with 100 nM of $MCa_b$/Strept-Cy3 complex. The specific binding of the triturated ryanodine to the sarcoplasmic reticulum vesicles was measured as described in the materials and methods. (−) represents the binding in the absence of MCa or of $MCa_b$/Strept-Cy3 complex. (B) Induction of calcium release by the sarcoplasmic reticulum vesicles, with 100 nM of $MCa_b$/Strept-Cy3 complex. 1 and 2 represent the addition of, respectively, 50 and 20 µM of $CaCl_2$ (final concentration), while 3 and 4 represent the consecutive addition of 20 µM of $CaCl_2$. A23187 was added at a final concentration of 4 µM.

FIG. 12 shows that the $MCa_b$/Strept-Cy3 complexes conserve the ability to stimulate [$^3$H]-ryanodine binding to heavy sarcoplasmic reticulum vesicles (panel A) and to induce $Ca^{2+}$ release from these vesicles (panel B).

The slower kinetics of $Ca^{2+}$ release, induced by the $MCa_b$/Strept-Cy3 complex, in comparison with maurocalcine alone, is an indicator of slightly reduced efficiency (FIG. 12B). This difference probably comes from a reduced accessibility of the $MCa_b$/Strept-Cy3 complex at the site of active maurocalcine binding to the RyR1 receptor, because of the hindrance due to the Strept-Cy3 (MW of streptavidin of 60 000 Da compared with 4108 Da for $MCa_b$).

The results obtained with the $MCa_b$/Strept-Cy3 complex validate the experimental approach used to identify maurocalcine-derived peptides devoid of any pharmacological effect on the RyR1 receptor.

Figure 13:
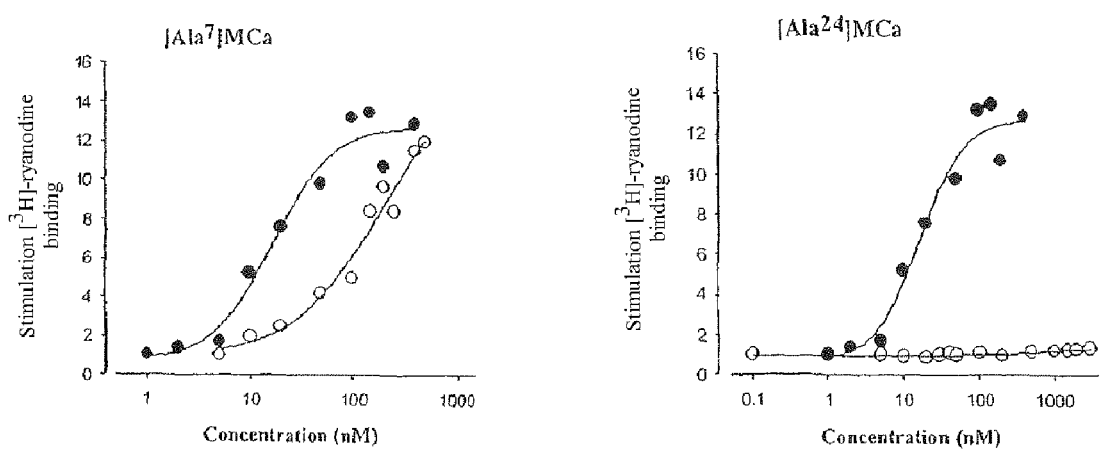
FIG. 13 illustrates the effect of the maurocalcine variants L7A and R24A, biotinylated and complexed with Strept-Cy3, on the RyR1 receptor. The stimulation of the [$^3$H]-ryanodine binding was measured at increasing concentrations of complexes. The specific binding of the triturated ryanodine to the sarcoplasmic reticulum vesicles was measured as described in materials and methods.

FIG. 13 shows that, among the maurocalcine variants capable of penetrating into cells and transporting substances of interest, the L7A mutant is less active on the RyR1 receptor than $MCa_b$/Strept-Cy3, whereas the R24A mutant is inactive.

EXAMPLE 4

Figure 14:
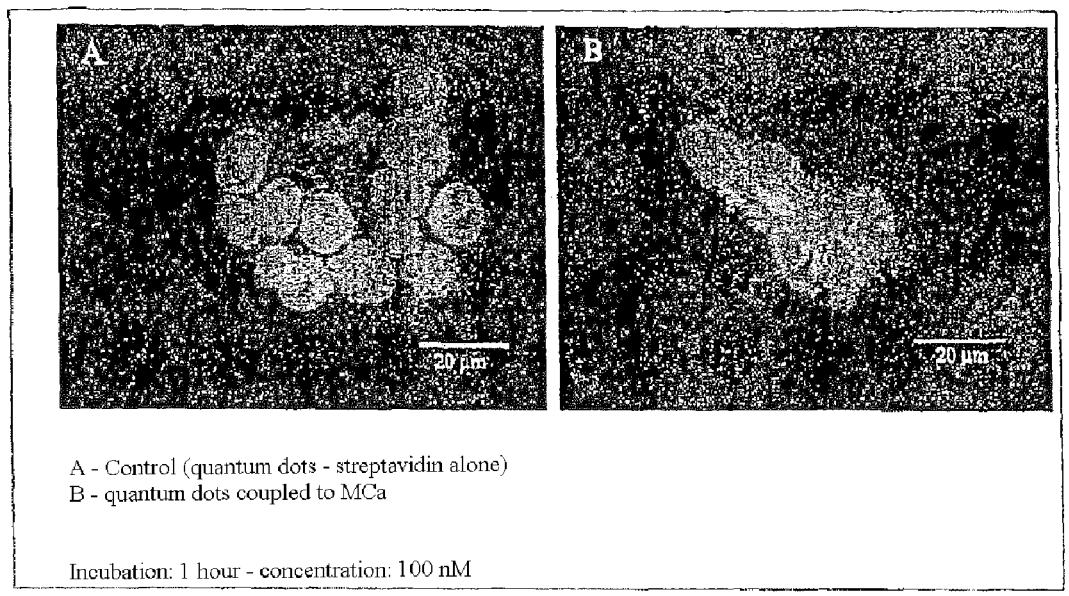
FIG. 14 illustrates the use of maurocalcine for the cellular penetration of nanoparticles. A. HEK293 cell cultures were incubated for 1 hour with 100 nM of maurocalcine coupled to nanoparticles (QDOT®, QUANTUMDOT CORPORATION), and the cells were then fixed and analyzed by confocal microscopy. Cultures of cells treated under the same conditions with QDOT® coupled to streptavidin serve as a control.

Use of Maurocalcine or of Derived Peptides for the Cellular Penetration of Nanoparticles Biotinylated maurocalcine was coupled to streptavidin-conjugated nanoparticles (QDOT®, QUANTUMDOT CORPORATION), according to the protocol recommended by the supplier. Streptavidin-coupled nanoparticles alone (QDOT® streptavidin conjugate, QUANTUMDOT CORPORATION) were used as a control. The nanoparticles have a diameter of 10 to 15 nM and are each coupled to 5 to 7 streptavidin molecules. HEK293 cell cultures were incubated for 1 hour with 100 nM of maurocalcine coupled to nanoparticles (QDOT®, QUANTUMDOT CORPORATION) or nanoparticles coupled to streptavidin alone, and the cells were then fixed and analyzed by confocal microscopy, as described in Example 1. FIG. 14 shows that maurocalcine allows cellular penetration of the nanoparticles.

What is claimed is:

1. A method of intracellular delivery of a substance of interest, comprising the step of using a maurocalcine-derived peptide vector for transporting said substance of interest into cells, wherein said maurocalcine-derived peptide vector consists of the following amino acid sequence (I):

$Z-X_1-X_2-X_3-X_4-X_5-X_6-X_7-X_8-X_9-X_{10}-X_{11}-X_{12}-X_{13}-X_{14}-X_{15}-X_{16}-X_{17}-X_{18}-X_{19}-X_{20}-X_{21}-X_{22}-X_{23}-X_{24}-X_{25}-X_{26}-Z'$ (I), in which:

$X_1$, $X_7$, $X_{12}$ and $X_{26}$ each represent a cysteine, $X_9$ represents a serine or a glycine, $X_{10}$, $X_{11}$, $X_{13}$, $X_{14}$, $X_{21}$ and $X_{22}$ represent a lysine or an arginine, $X_{15}$ represents an arginine or is different from an arginine and a lysine, $X_{16}$ represents a glycine, $X_{17}$ represents a threonine, $X_{18}$ represents an asparagine, $X_{19}$ represents an isoleucine or a proline, $X_{20}$ represents a glutamic acid, and $X_2$, $X_3$, $X_4$, $X_5$, $X_6$, $X_8$, $X_{23}$, $X_{24}$ and $X_{25}$ are absent, wherein one of $X_{15}$, $X_{16}$, $X_{17}$, $X_{18}$, $X_{19}$ and $X_{20}$ may be an alanine, Z' represents an arginine or a lysine, Z is either absent or corresponds to the following amino acid sequence (II):

$Z_1-Z_2-Z_3-Z_4-Z_5-Z_6-Z_7-Z_8-Z_9-Z_{10}-Z_{11}-Z_{12}-Z_{13}-Z_{14}-Z_{15}-Z_{16}-Z_{17}-Z_{18}-Z_{19}-Z_{20}-Z_{21}-Z_{22}-Z_{23}-Z_{24}-Z_{25}-Z_{26}-Z_{27}-Z_{28}-Z_{29}-Z_{30}-Z_{31}-Z_{32}-Z_{33}-Z_{34}-Z_{35}$ (II), in which:

$Z_{19}$ represents a glycine or is absent, $Z_{20}$ represents an aspartic acid or is absent, $Z_{21}$ represents a cysteine or is absent, $Z_{23}$ representda leucine or is absent, $Z_{24}$ represents a proline or is absent, $Z_{25}$ represents a histidine or is absent, $Z_{26}$ represents a leucine or is absent, $Z_{27}$ represents an arginine or a lysine, or is absent, $Z_{28}$ represents a leucine, an arginine or a lysine, or is absent, $Z_{29}$ represents a cysteine, $Z_{30}$ represents an arginine or a lysine, $Z_{32}$ represents a glutamic acid, $Z_{33}$ represents an asparagine or an aspartic acid, $Z_{34}$ represents an arginine, a lysine or an asparagine, and $Z_{35}$ represents an aspartic acid, wherein one of $Z_{28}$ and $Z_{34}$ is a lysine or an arginine, wherein one of $Z_{20}$, $Z_{23}$, $Z_{24}$, $Z_{25}$, $Z_{26}$, $Z_{27}$ $Z_{28}$, $Z_{32}$, $Z_{33}$ and $Z_{35}$ may be an alanine, wherein $Z_1$ to $Z_{18}$, $Z_{22}$ and $Z_{31}$ are absent, and wherein $Z_{29}$, $Z_{30}$, $Z_{32}$, $Z_{33}$, $Z_{34}$ and $Z_{35}$ are always present, either alone or in combination with one of $Z_{27}$ and $Z_{28}$; $Z_{21}$, $Z_{23}$ $Z_{24}$, $Z_{25}$, $Z_{26}$ $Z_{27}$ and $Z_{28}$; $Z_{20}$, $Z_{21}$, $Z_{23}$, $Z_{24}$, $Z_{25}$, $Z_{26}$ $Z_{27}$ and $Z_{28}$; or $Z_{19}$, $Z_{20}$, $Z_{21}$, $Z_{23}$, $Z_{24}$, $Z_{25}$, $Z_{26}$, $Z_{27}$ and $Z_{28}$, and wherein said peptide vector is different from the sequence SEQ ID NO: 1.

2. The method according to claim 1, wherein said $Z_{27}$ and/or $Z_{28}$ represent an arginine or a lysine.

3. The method according to claim 1, wherein said $Z_{27}$ and $Z_{30}$ each represent a lysine.

4. The method according to claim 1, wherein said peptide of sequence (I) is selected from the group consisting of the sequences SEQ ID NO: 2 and SEQ ID NO: 7 to 25.

5. The method according to claim 1, wherein said peptide vector consists of D amino acids.

6. The method according to claim 1, wherein said peptide vector is coupled to an appropriate label.

7. The method according to claim 1, wherein the peptide vector is coupled to particles.

8. The method according to claim 7, wherein said particles comprise the substance of interest.

9. The method according to claim 1, wherein said substance of interest is a pharmacologically active substance whose target is intracellular.

10. The method according to claim 1, wherein said substance of interest is a ligand of an intracellular component to be detected.

11. The method according to claim 10, wherein said ligand is an antibody or a functional fragment of an antibody directed against said intracellular component.

12. The method according to claim 1, wherein said peptide vector consists of SEQ ID NO: 7.

* * * * *